(12) United States Patent
Wright

(10) Patent No.: US 10,386,338 B2
(45) Date of Patent: Aug. 20, 2019

(54) DNA/RNA PEMS MICROCANTILEVER PROBE FOR DETECTION OF VIRAL INFECTION AND DETECTION OF GENETIC VARIANTS

(71) Applicant: Cynthia Rena Wright, Huntsville, AL (US)

(72) Inventor: Cynthia Rena Wright, Huntsville, AL (US)

( * ) Notice: Subject to any disclaimer, the term of this patent is extended or adjusted under 35 U.S.C. 154(b) by 0 days.

(21) Appl. No.: 16/014,878

(22) Filed: Jun. 21, 2018

(65) Prior Publication Data
US 2019/0128853 A1    May 2, 2019

Related U.S. Application Data

(60) Provisional application No. 62/578,638, filed on Oct. 30, 2017.

(51) Int. Cl.
| | | |
|---|---|---|
| *G01N 33/66* | (2006.01) | |
| *B82Y 35/00* | (2011.01) | |
| *G01N 29/24* | (2006.01) | |
| *B82Y 5/00* | (2011.01) | |

(52) U.S. Cl.
CPC ............ *G01N 29/2437* (2013.01); *B82Y 5/00* (2013.01); *B82Y 35/00* (2013.01); *G01N 2291/0255* (2013.01); *G01N 2291/0256* (2013.01); *G01N 2291/0427* (2013.01)

(58) Field of Classification Search
CPC ..... G01N 29/2437; G01N 33/66; B82Y 35/00
See application file for complete search history.

(56) References Cited

U.S. PATENT DOCUMENTS

| | | |
|---|---|---|
| 5,547,667 A | 8/1996 | Angelucci et al. |
| 5,824,805 A | 10/1998 | King et al. |
| 6,218,160 B1 | 4/2001 | Duan |
| 6,512,101 B1 | 1/2003 | King et al. |

(Continued)

FOREIGN PATENT DOCUMENTS

WO    2016161333    10/2016

OTHER PUBLICATIONS

Gianluca Palmara, Microcantilever-Based Sensing Arrays for Evaluation of Biomolecular Interactions, hhtp://porto.polito.it/2639290/1/PhD_Thesis_Gianluca_Palmara_pdf, pp. 38-42, Apr. 2016.

(Continued)

*Primary Examiner* — Tracy Vivlemore
*Assistant Examiner* — Nam P Nguyen

(57) ABSTRACT

The present invention relates to a piezoelectric mechanical system (PEMS) microcantilever sensor that both detects the presence of viral RNA in an aqueous solution, such as a blood sample. The method provides for the formation of the sensor by attaching RNA, DNA, or an antibody to the microcantilever sensor surface via a hydrazone or an oxime chemical bond. The method provides for the detection of viral RNA viruses and viral DNA viruses upon the chemical binding/bonding of single-stranded viral nucleic acid to the microcantilever sensor surface. The method provides for the detection of DNA cancer mutations or variants that have been identified in a cancer cell upon the chemical binding/bonding of single-stranded DNA to the microcantilever sensor surface.

7 Claims, 22 Drawing Sheets

(56) References Cited

U.S. PATENT DOCUMENTS

| | | | |
|---|---|---|---|
| 8,741,663 B2 | 6/2014 | Yang | |
| 9,012,148 B2 | 4/2015 | Han | |
| 9,013,690 B1* | 4/2015 | Chou | B82Y 15/00 |
| | | | 356/317 |
| 9,206,216 B2* | 12/2015 | Etienne | C07H 19/10 |
| 9,274,087 B2 | 3/2016 | Shih et al. | |
| 2005/0112621 A1 | 5/2005 | Kim et al. | |
| 2006/0008830 A1* | 1/2006 | Slattum | C07H 21/04 |
| | | | 435/6.14 |
| 2007/0089515 A1 | 4/2007 | Shih et al. | |
| 2007/0116607 A1* | 5/2007 | Wang | B01L 3/502715 |
| | | | 422/83 |
| 2010/0037682 A1 | 2/2010 | Xu | |
| 2010/0088039 A1 | 4/2010 | Yang et al. | |
| 2013/0266573 A1 | 10/2013 | Old et al. | |
| 2015/0376700 A1* | 12/2015 | Schnall-Levin | C12Q 1/6883 |
| | | | 506/4 |

OTHER PUBLICATIONS

Caroline Viguier, Carol Lynam, Richard O'Kennedy, Trends and Perspectives in Immunosensors, http://epubs.surrey.ac.uk/808331/10/trends-and-perspectives-in-immunosensors-correctedversion-july2011.pdf.

Lu-Hsun Cheng, Ya-Chun Chang, Wen-Chi Hu, et al., Using a CMOS-BioMEMS Cantilever Sensor for Orchid Virus Detection, 15th Intl. conference on Miniaturized Systems for Chemistry and Life Sciences, Oct. 2-6, 2011, Seattle, Washington, USA.

Lu-Hsun Cheng, Ya-Chun Chang, Wen-Chi Hu, Hsin-Hao Liao, Hann-Huei Tsai, Ying-Zong Juang and Yen-Wen Lu, Using a CMOS-BIOMEMS Cantilever Sensor for Orchid Virus Detection, 15th International Conference on Miniaturized Systems for Chemistry and Life Sciences, 2011, pp. 623-625, V.1, MicroTAS 2011, Seattle, Washington, USA.

Caroline Viguier, Carol Lynam, Richard O'Kennedy, Trends and Perspectives in Immunosensors, Antibodies Applications and New Developments, 2012, pp. 184-208, Bentham Science Publishers, Emirate of Sharjah, United Arab Emirates.

Anja Biosen and Thomas Thundat, Design & fabrication of cantilever array biosensors, Materials Today, Sep. 2009, V. 12, N. 9, pp. 32-38, Elsevier, New York City, NY, USA.

Priscila M. Kosaka, Valerio Pini, Montserrat Calleja, Javier Tamayo, Ultrasensitive detectection of HIV-1 p24 antigen by a hybrid nanomechanical-optoplasmonic platform with potential for detecting HIV-1 at first week after infection, PLOS ONE, Feb. 15, 2017, V. 12, N. 2, pp. 1-13, Public Library of Science, San Francisco, California, USA.

Diagnosis of HIV Infection in Infants and Children, Guidelines for the Use of Antiretroviral Agents in Pediatric HIV Infection, AIDS Info, Nov. 15, 2017, pp. 1-20, National Institute of Health, Rockville, Maryland, USA.

Alexander Papra, Nikolaj Gadegaard, Niels B. Larsen, Characterization of Ultrathin Poly(ethylene glycol) Monolayers on Silicon Substrates, Langmuir, 2001, vol. 17, pp. 1457-1460, American Chemical Society, Washington D.C, USA.

Francesca Cecchet, Benoit de Meersman, Sophie Demounstier-Champagne, Bernard Nysten, and Alain M. Jonas, One Step Growth of Protein Antifouling Surfaces: Monolayers of Poly(ethylene oxide) (PEO) Derivatives on Oxidized and Hydrogen-Passivated Silicon Surfaces, Langmuir, 2006, V. 22, pp. 1173-1181, American Chemical Society, Washington D.C, USA.

Roza Trzcinska, Katarzyna Balin, Jerzy Kubacki, Magdalena E. Marzec, Roman Pedrys, Jacek Szade, Jerzy Silberring, Andrzej Dwarak, Barbara Trzebicka, Relevance of the Poly(ethylene glycol) Linkers in Peptide Surfaces for Proteases Assays, Langmuir, 2014, V. 30, pp. 5015-5025, American Chemical Society, Washington D.C, USA.

Thien Dien To, Anh Tuan Nguyen, Khoa Nhat Thanh Phan, An Thu Thi Truong, Tin Chanh Duc Doan and Chien Mau Dang, Modification of silicon nitride surfaces with GOPES and APTESE for antibody immobilization: computational and experimental studies, Advances in Natural Sciences: Nanoscience and Nanotechnology, 2015, V. 6, N.4, pp. 1-8, IOP Publishing and Vietnam Academy of Science & Technology, Hanoi, Vietnam.

Katanchalee Vacheethasanee, Shuwu Wang, Yongzing Qui, Roger E. Marchant, Poly(ethylene oxide) surfactant polymers, Journal of Biomaterials Science, Polymer Edition, 2004, V. 15, N. 1, pp. 95-110, Taylor and Francis, London, UK.

Michel Rosso, Ai T. Nguyen, Ed De Jong, Jacob Baggerman, Jos M. J. Paulusse, Marcel Giesbers, Remko G. Fokkink, Willem Norde, Karin Schroen, Cees J. M. Van Rijn, and Han Zuilof, Protein-Repellent Silicon Nitride Surfaces: UV-Induced Formation of Oligoethylene Oxide Monolayers, Applied Materials & Interfaces, 2011, V. 3, pp. 697-704, American Chemical Society, Washington D.C, USA.

D. Leckband, S. Sheth, A. Halperin, Grafted poly(ethylene oxide) brushes as nonfouling surface coatings, Journal of Biomaterials Science, Polymer Edition, 1999, V. 10, N. 10, pp. 1125-1147, Taylor and Francis, London, UK.

Sangkyu Lee, Jongyun Cho, Yeolho Lee, Sangmin Jeon, Hyung Joon Cha, Wonkyu Moon, Measurement of Hepatitis B Surface Antigen Concentrations Using a Piezoelectric Microcantilever as a Mass Sensor, Journal of Sensors, 2012, V. 2012, pp. 1-6, Hindawi, Cairo, Egypt.

Feifei Cheng, Li Su, Cheng Qian,Circulating tumor DNA: a promising biomarker in the liquid biopsy of cancer, Oncotarget, V. 7, N. 30, May 19, 2016, pp. 48823-48841, Impact Journals, Orchard Park, NY, USA.

Chetan Bettegowda, et al., Detection of Circulating Tumor DNA in Early-and Late-Stage Human Malignancies, Science Translational Medicine, Feb. 19, 2014, V. 6, N. 224, pp. 1-25, American Association for the Advancement of Science, Washington D.C., USA.

Blanca Valle, The Epigenetic Marks of Circulating Cell-Free DNA (cfDNA), What is Epigenetics, Sep. 16, 2016, New York, New York, USA.

Jin yan Tang, Jamal Temsamani and Sudhir Agrawal, Self-stabilized antisense oligodeoxynucleotide phosphorothioates: properties and anti-HIV activity, Nucleic Acids Research, 1993, vol. 21, No. 11 2779-2735, Oxford University Press.

He Cheng, et al., Analysis of ctDNA to predict prognosis and monitor treatment responses in metastatic pancreatic cancer patients, International Journal of Cancer, V. 140, pp. 2344-2350, UICC, Geneva, Switzerland.

Sarah B. Ng, et. al, Individualised multiplexed circulating tumour DNA assays for monitoring of tomour presence in patients after colorectal cancer surgery, Scientific Reports, Jan. 19, 2017, V. 7, Article No. 40737 (2017), Springer Nature, Cham, Switzerland.

Hydrazides—an overview, Sciencedirect.com, Accessed: May 5, 2018, pp. 1-10, Elsevier, New York City, NY, USA.

Stanislav Volik, Miguel Alcaide, Ryan D. Morin, et al., Cell-free DNA (cfDNA): Clinical Significance and Utility in Cancer Shaped by Emerging Technologies, Molecular Cancer Research, Oct. 2016, V. 14, N. 10, pp. 898-908, American Association for Cancer Research, Philadelphia, PA, USA.

Christian Drosten, Stephan Gottig, Stefan Schilling, et al., Rapid Detection and Quantification of RNA of Ebola and Marburg Viruses, Lassa Virus, Crimean-Congo Hemorrhagic Fever Virus, Rift Valley Fever Virus, Dengue Virus, and Yellow Fever Virus by Real-Time Reverse Transcription—PCR, Journal of Clinical Microbiology, Jul. 2002, V. 40, N. 7, pp. 2323-2330, American Society for Microbiology, Washington, DC, USA.

Leszek Lisowski, Menashe Elazar, Kirk Chu, et al., The antigenomic (negative) strand of Hepatitis C Virus is not targetable by shRNA, Nucleic Acids Research, 2013, V. 41, N. 6, pp. 3688-3698, Oxford University Press, Oxford, England, UK.

John J. Turner, Martin Fabani, Andrey A. Arzumanov, et al., Targeting the HIV-1 RNA leader sequence with synthetic oligonucleotides and siRNA: Chemistry and cell delivery, Biochimica et Biophysica Acta, 2006, V. 1758 pp. 290-300, Elsevier, New York City, NY, USA.

F. Duconge and J.J. Toulme, In vitro selection identifies key deterinants for loop-loop interactions: RNA aptamers selective

(56) References Cited

OTHER PUBLICATIONS for the TAR RNA element of HIV-1, RNA Journal, 1999, V.5, pp. 1605-1614, Cambridge University Press, Cambridge, England, UK.
Daniel Pietrasz, Nicolas Pecuchet, Fanny Garlan, et al., Plasma Circulating Tumor DNA in Pancreatic Cancer Patients Is a Prognostic Marker, Clinical Cancer Research, 2017, V. 23, N. 1, pp. 116-123, American Association for Cancer Research, Philadelphia, PA, USA.
Xiao Han, Junyn Wang, Yingli Sun, Circulating tumor DNA as biomarkers for cancer detection, Genomics Preteomics Bioinformatics, 2017, V. 15, pp. 59-72, Elsevier, New York City, NY, USA.
Nidhi Maheshwari, Gaurav Chatterjee, V. Ramgopal Rao, A technology overview and applications of Bio-MEMS, Journal of ISSS, Sep. 2014, V. 3, N. 2, pp. 39-59, Institute of Smart Structures and Systems, India.
Yee Lam, Nehal I. Abu-Lail, et al., Using microcantilever deflection to detect HIV-1 envelope glycoprotein gp120, Nanomedicine: Nanotechnology, Biology, and Medicine, 2006, V. 2, pp. 222-229, Elsevier, New York City, NY, USA.
Detection of BRCA1/2 mutations in circulating tumor DNA from patients with ovarian cancer, Oncotarget, V. 8, N. 60, Sep. 8, 2017, pp. 48823-48841, Impact Journals, Orchard Park, NY, USA.
Y Arntz, JD Seelig, HP Lang, et al., Label-free protein assay based on a nanomechanical cantilever array, Nanotechnology, 2003, V. 14, pp. 86-90, Institute of Physics Publishing, Bristol, UK.
Nitin S Kale, Manoj Joshi, P Nageswara Rao, S Mukherji, V Ramgopal Rao, Bio-functionalization of silicon nitride-based piezoresistive microcantilevers, Sadhana, Aug. 2009, V. 34, N. 4, pp. 591-597, Indian Academy of Sciences, Bangalore, Karnataka, India.
Mark A. Lifson, Mehmet Ozgun Ozen, Fatih Inci, et al., Advances in biosensing strategies for HIV-1 detection, diagnosis, and therapeutic monitoring, Advanced Drug Delivery Reviews, 2016, V. 103, pp. 90-104, Elsevier, New York City, NY, USA.
Shuaipeng Wang, Jingjing Wang, Yinfang Zhu, et al., A new device for liver cancer biomarker detection with high accuracy, Sensing and Bio-Sensing Research, 2015, V. 4, pp. 40-45, Elsevier, New York City, NY, USA.
Melissa I. Chang., Porntula Panorchan, Terrence M. Dobrowsky, et al., Single-Molecule Analysis of Human Immunodeficiency Virus Type 1 gp120-Receptor Interactions in Living Cells, Journal of Virology, Dec. 2005, pp. 14748-14755, American Society for Microbiology, Washington, DC, USA.
Samira Aegh, Nader Jalili, Srinivas Sridhar, A Self-Sensing Piezoelectric MicroCantilever Biosensor for detection of Ultrasmall Adsorbed Masses: Theory and Experiments, Sensors 2013, 13, 6089-6108; doi:10.3390/s130506089, Basel Switzerland.
F. Duconge, JJ Toulme, In vitro selection identifies key determinants for loop-loop interactions: RNA aptamers selective for the TAR RNA element of HIV-1, RNA (1999) 5: 1605-1614, Cambridge University Press, USA.
Tao Yuan, Chaodong Li, Pingging Fan, An Equivalent circuit of Longitudinal Vibration for a Piezoelectric Structure with Losses, Sensors, Apr. 2018; 18(4): 947, 10.3390/S18040947, Basel, Switzerland.
R. James Christie, Diana J. Anderson, David W. Grainger, Comparison of Hydrazone Heterobifunctional Crosslinking Agents for reversible Conjugation of Thio-Containing Chemistry, Bioconjug Chem. Oct. 20, 2010: 21 (10), 1779-1787. doi: 10.1021/bc100049c.
Mohammad Rashidian, Homammad M. Mahmood, Rachit Shah, Jonathan K. Dozier, Carston R. Wagner, Mark D. Distefano, A Highly Efficient Catalyst for Oxime Ligation and Hydrazone-Oxime Exchange Suitable for Bioconjugation, Bioconjug Chem., 2013, 24 (3), 333-342. doi:10.1021/bc3004167.
Jett Kalia, Ronald T. Raines, Hydrolytic Stability of Hydrazones and Oximes, Agnew Chem Int Ed Engl. 2008; 47(30): 7523-7526. doi: 10.1002/anie.200802651.

\* cited by examiner

DNA/RNA PEMS MICROCANTILEVER PROBE FOR DETECTION OF VIRAL INFECTION AND DETECTION OF GENETIC VARIANTS

CROSS-REFERENCE TO RELATED APPLICATIONS

The application claims priority to U.S. Provisional Application 62/578,638 filed on Oct. 30, 2017 naming John Bequette and Cynthia R. Wright as co-inventors.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM

Not applicable.

STATEMENT REGARDING PRIOR DISCLOSURES BY THE INVENTOR OR JOINT INVENTOR

The inventor did not disclose the invention herein prior to the 12 month period preceding the filing of this provisional application.

BACKGROUND OF THE INVENTION

(1) Field of the Invention

The invention relates generally to a test probe and method of using the probe to detect certain viral infections and to detect certain genetic variants utilizing a nucleic acid molecular probe. Additionally, the method herein discloses a novel way of attaching an antibody or nucleic amino to a PEMS microcantilever probe that reduces the likelihood of improper attachment via the antibody active site, and establishes a more stable attachment with the PEMS microcantilever probe.

HIV-1 detection and diagnosis is performed by certain tests and methods that detect the presence of antibodies produced by an individual following infection. These antibodies often are not detectable in a newly infected individual for up to six months post transmission. Upon initial HIV infection, HIV RNA is detectable in a patient's blood. A device or method of testing for HIV RNA will enable detection of the virus upon initial infection which may be prior to the infected individual's production of detectable antibodies. Additionally, the blood of infants born to HIV-infected mothers includes antibodies to HIV irrespective of whether the infant is infected with the virus. A molecular probe that detects HIV RNA instead of HIV antibodies will allow infants born to HIV-infected mothers to be tested for the presence of HIV RNA immediately after birth so that infected infants can be identified and treatment initiated as soon as possible.

This test probe allows for detection of viral infection at the point of patient contact without laboratory processing, such as PCR and ELISA. Laboratory processing may not be available in certain undeveloped regions such as Guinea, Liberia, or other African countries. For example, HIV and Ebola, or other hemorrhagic viral infections are known to infect individuals in remote areas, areas lacking adequate resources to detect infection. The probe herein allows the detection of viral RNA and/or viral DNA in a patient's aqueous specimen without expensive laboratory equipment and eliminates any risk of improper specimen handling during transportation of the specimen to a laboratory.

Currently, cancers, such as colon and ovarian cancer, are screened using evasive testings including, but not limited to, colonoscopy and biopsy. Colonoscopy and biopsy are expensive to perform and medically invasive typically requiring sedation at an outpatient surgery facility. A molecular probe and a method of using the probe that utilizes just a couple drops of a patient's blood will reduce the financial costs and the risks to a patient's health associated with colonscopy and biopsy. Some cancers, including pancreatic, ovarian, and lung, do not have a routine method of screening. If a patient is suspected of having pancreatic, ovarian, or lung cancer, then that patient is subjected to a number of invasive tests. There is a need for a testing method that will permit routine screening of pancreatic, ovarian, and lung cancer in a non-invasive method and at a reasonable price. Certain cancer mutations respond favorably to certain treatment modalities. The invention herein includes a blood test to detect genetic variants/mutations associated with certain cancers. This allows a single test to screen for multiple cancer genetic mutations so that a treatment regime can be tailored to the individual patient.

(2) Disclosure of the Prior Art

Current HIV testing requires a patient to provide a blood sample that is sent to a lab for testing. The lab performs immunoabsorbent assay tests, such as enzyme-linked immunoabsorbent assay (ELISA), that detect the presence of certain antibodies in the blood. During the ELISA test, a lab technician adds blood from the sample to a petri dish containing HIV antigen. If the blood contains antibodies to HIV, the HIV will bind to the antibodies. The technician checks for HIV antibody binding by adding an enzyme that causes the petri dish to change color of HIV is present. ELISA testing is typically unable to detect HIV-1 infection during the first six months following initial infection because antibodies are present in undetectable levels. ELISA testing is very safe, but a drawing blood for the test may cause a person to feel lightheaded or faint, infection may occur at the site the needle was inserted, bruising at the site the needle was inserted is common, and problems may arise for those on blood thinners or anticoagulant medications. Additionally, ELISA testing is performed in advanced laboratories and may be cost prohibitive in poor regions of the world.

Nucleic-acid-based tests amplify and detect one or more of several target nucleic acid sequences in specific HIV genes, such as HIV-1 GAG, HIV-II GAG, IV-env, or the HIV-pol. Because tests are expensive, blood samples are first screened by pooling some 8 to 24 samples together; if the pool tests positive, each sample is retested individually. In the Quantiplex bDNA or branched DNA test, blood plasma is centrifugated to concentrate the virus, which is then opened to release its RNA. Special oligonucleotides that bind to viral RNA and to certain oligonucleotides bound to the wall of the vessel are added. In this way, viral RNA is fastened to the wall. Then new oligonucleotides that bind at several locations to this RNA are added, and other oligonucleotides that bind at several locations to those oligonucleotides. Finally, oligonucleotides that bind to the last set of oligonucleotides and that are bound to an enzyme are added causing a color reaction by the enzymatic reaction, which allows quantification of the viral RNA in the original sample. This test is used on viral loads greater than 25,000 copies per milliliter. This process is expensive, requires a lot of lab space, a lot of lab time, and is time consuming. Additionally, this method requires a blood sample be obtained via veinipuncture, subjecting the patient to the possibility of fainting, infection, bruising, and may not be acceptable for some patients prescribed anticoagulants.

A method of detecting HIV-1, and HIV-2, that is affordable, sensitive, specific, user friendly, robust and rapid, equipment-free, and deliverable is needed. This method allows for testing of either HIV RNA or HIV antigens. HIV is a single-stranded RNA virus that is enveloped within an infected patient's own cells. Despite being enveloped, patients infected with HIV have HIV single-stranded RNA circulating within their circulatory system. The test and method herein comprises a PEMS microcantilever sensor that detects HIV single-stranded RNA that is circulating within the patient's blood. The test and method is relatively affordable, it is sensitive to very low HIV single-stranded RNA concentrations, is easy to use and does not require a laboratory, may be delivered to remote locales without refrigeration, and may be stored within reasonable limits for up to two years without refrigeration.

Hepatitus C virus (HCV) infects more than 150 million people worldwide, with infection rates of up to 20% in some countries. HCV infection may be characterized by extremely high numbers of blood virons, especially during active infection. HCV is highly conserved allowing a single probe to effectively detect and quantify infection. Today, diagnosing Hepatitis C begins with an antibody test. Antibodies to HCV can be detected in the blood, usually within two or three months after the virus enters the body. Upon confirmation of the presence of HCV antibodies, a qualitative HCV RNA test is performed to determine if the actual virus is in a person's bloodstream. Quantitative HCV RNA may also be performed to determine the viral load of HCV in a person's blood. The following methods are used to detect HCV RNA in a patient's blood sample: TMA (transcription-mediated amplification), PCR (polymerase chain reaction), and bDNA (branched DNA). These tests are also performed after infection to ascertain disease progression and the effectiveness of certain treatment modalities. These tests are expensive to perform and require a laboratory setting.

Ebola virus is a hemorrhagic virus found in certain parts of Africa. Individuals infected with Ebola present Ebola virus-specific immunoglobulin (Ig) G in their blood and body fluids. Currently, ReEBOV Antigen Rapid Test kit for Ebola is utilized to test for Ebola infection. ReEBOV Antigen Rapid Test diagnosis of Ebola virus disease requires transport of venepuncture blood to field biocontainment laboratories for testing by real-time RT-PCR, resulting in delays that complicate patient care and infection control efforts. Therefore, an urgent need exists for a point-of-care rapid diagnostic test for this disease. The assay disclosed herein allows for immediate detection of Ebola virus in a biological sample without the need for venepuncture blood and transport to a biocontainment lab. The probe herein allows Ebola infection to be detected in a single drop of blood at the point of patient contact, allowing for immediate removal of the infected patient from the community, decreasing the likelihood of infection of others in the community.

More than 1.6 million individuals in the United States will be afflicted with cancer each year. Serum-based protein biomarkers such as carcinoma antigen-125, carcinoembryonic antigen, and prostate-specific antigen are commonly used as biomarkers for detection of cancer in serum. These biomarkers are found in serum of individuals without cancer, albeit at lower concentrations, and they may not be elevated in some with advanced cancers. Genomic research has identified that patients with certain cancers, including ovarian and colorectal cancers, have detectable levels of certain circulating tumor DNA in their blood. The method of identifying the mutated cancer DNA involves many steps including PCR with DNA agarose gel identification, which is time consuming, prone to error, and are labor intensive and time consuming for routine use. Today, painful biopsy and expensive testing are the only methods utilized for cancer detection. There does not exists a method of rapid blood screening for the presence of DNA cancer markers in blood. Today, ovarian and colorectal cancer are typically detected by diagnostic imaging or biopsy.

Certain drugs are known to improve the effectiveness of certain cancer treatments. Some women with breast and/or ovarian cancer are known to have mutations in their BRCA1 and/or BRCA2 gene. Scientists have identified that women with a BRCA1 or BRCA2 mutation generally responded better to chemotherapy before surgery without carboplatin (a chemotherapeutic gent used to treat ovarian cancer, lung cancer, head and neck cancer, brain cancer, and neuroblastoma), while women without a BRCA1 or BRCA2 mutation had better outcomes when carboplatin was added to the chemotherapy regimen. Currently, PCR is performed to ascertain whether a patient has a BRCA 1 or BRCA2 mutation. The test probe disclosed herein can be used instead of PCR to identify whether a cancer patient has a particular mutation of the BRCA1 or BRCA 2 gene. The test probe herein may be utilized as a method of screening cancer mutations in order to customize cancer treatment to an individual.

The prior art teaches an apparatus for detection of chemical or biological agents utilizing a cantilever probe array. Adams (US 2006/0257286 A1) discloses a cantilever probe array having a plurality of self-sensed cantilevered probes, at least one chemical-sensitive coating material applied to at least one cantilevered probe in the cantilevered probe array, and an interface circuit that is coupled to the cantilevered probe array. At least one cantilevered probe in the cantilevered probe array exhibits a shifted cantilevered probe response when the cantilevered probe array is exposed to the target chemical species and the interface circuit actuates the cantilevered probe. Adams teaches a hand held chemical detection system and a method of operation of said detection system. The device of Adams is designed to detect certain chemical and or biological agents in the air being tested. Adams includes inlet port 62 and outlet port 64 to allow ingress and egress, respectively, of chemical species 12 or a by-product therefrom into the device. The cantilever probe arrays taught in Adams include either: (1) probes manufactured with small differences in cantilever lengths or thickness [0051] or (2) probes manufactured so that they are nominally the same size and thickness but varying the area coated with chemically-sensitive coating material 34. Adams utilizes the difference in either probe size or probe area coated with coating material 34 to create a detectable separation in resonant frequency. The invention herein differs significantly from Adams.

Cantilevers have been used to detect binding properties of HIV. "Using microcantilever deflection to detect HIV-1 envelope glycoprotein gp 120", Lam et al., Nanomedicine: Nanotechnology, Biology, and Medicine 2 (2006) 222-229, doi:10.1016/j.nano.2006.10.002, teaches a single cantilever using atomic force microscopy (AFM) to detect deflections upon specific binding of gp120 to cantilevers decorated on one side with monoclonal antibodies A32 or T8. Lam et al. discloses a method of the detection of gp120 using AFM comprising obtaining a base reading of a primed cantilever, subjecting said primed cantilever to a solution containing gp120, and obtaining a second reading upon binding of gp120 to the primed cantilever. An initial reading of the primed cantilever is obtained by placing a cantilever modified with antibodies in a commercially-available glass fluid cell, sealing said glass fluid cell with a clean glass substrate using a silicon O-ring, and measuring deflection by monitoring the position of a laser beam reflected from the free end of the microcantilever onto a photosensitive detector. Deflection voltage was recorded every 10 milliseconds using a data acquisition card. From the atomic force microscope. Next, the fluid cell is removed and a quantity of solution containing gp120 is introduced into the glass fluid cell. The glass fluid cell is then returned to the atomic force microscope and a second reading is obtained. This method requires an expensive atomic force microscope and highly experienced lab personnel. Additionally, to minimize variability between experiments, the method requires that cantilevers be obtained from neighboring positions on the cantilever wafer so that they will have similar spring constants and similar micro mechanical behavior. This method could not be employed for a large number of tests.

"Single-Molecule Analysis of Human Immunodeficiency Virus Type 1 gp120-Receptor Interactions in Living Cells", Chang et al., Journal of Virology, December 2005, p. 14748-14755, doi: 10.1128/JVI.79.23.14748-14755.2005, teaches the quantification of the binding interactions between HIV type 1 envelope glycoproteins and host cell surface receptors. This process utilizes a molecular force probe comprising a photodetector, photodetector mirror, recollimation lens, focus lens, and laser to detect cantilever movement. The cantilevers used by Chang are expensive, making the device expensive to the consumer. Chang uses a cantilever tip developed by Veeco Instruments that have a surface reactive non-specifically to biological and chemical agents. The cantilevers employed herein this application are cheaper and initially non-reactive to biological and chemical agents. Chang discloses priming the underside of a cantilever with gp120, gently bringing a host cell expressing either CD4 alone or in conjunction with CCRT, or both CD4 and CCR5 into contact with the primed cantilever, pulling the cantilever with a controlled reproach velocity, and monitoring the time-dependent force applied on the bond between gp120 and a single cell receptor and the time-dependent deformation of the cell membrane-bound proteins simultaneously. This method requires expensive equipment and a well-trained laboratory staff. The probe herein is coated with materials that non-selectively bind multiple biomolecules in addition to binding HIV-associated proteins/antibodies.

Shih et al. (U.S. Pat. No. 9,274,087 B2) discloses a piezoelectric microcantilever for sensing compounds or molecules. The piezoelectric microcantilever includes an immobilization layer, a non-piezoelectric layer and a piezoelectric layer. The sensor is capable of self actuation and detection. The piezoelectric layer is constructed from piezoelectric thin lead magnesium niobate-lead titanate film, a highly piezoelectric thin zirconate titanate film, or a highly piezoelectric lead-free film. Shih et al. discloses a number of methods of fabricating a PEMS microcantilever sensor so that the sensor will selectively bind to multiple biological compounds. However, the device of Shih et al. may not be used to detect biological compounds present in aqueous solutions. While the embodiments disclosed in Shih et al. may be used to detect certain antibodies, no method of detecting DNA and/or RNA is disclosed. Shih et al. attaches an antibody to the PEMS test surface via an amine bond. Amine bonds are weak and easily disassociate/hydrolyze in aqueous solution. Thus, amine bond linkages can not be utilized in aqueous solutions, and different chemical bond is necessary for the testing of aqueous samples. Additionally, amine bonds often cover the active sites of antibodies, thus, coupling an antibody to the PEMS surface via an amine bond is likely to involve improper couplings between an amine bond positioned within the active site, thus decreasing the binding activity of the antibody active site. A method of stable bonding with non-amine groups is desirable. Amine bonds are relatively weak and may disassociate in complex solutions, such as blood, urine, and saliva. An alternate bond to link binding agents to the PEMS surface would enable the device to maintain bonding with the binding agent. Additionally, Shih et al. fails to disclose any method of attaching either a DNA or RNA strand to a PEMS microcantilever. Due to lack of an amine functional group in either DNA or RNA, the method disclosed here does not permit the construction of a DNA/RNA probe. Differences in the chemical structure of nucleic acid and protein/antibodies limit the ability to create an antibody that will bind to DNA and/or RNA.

Kim et al. (US 2005/0112621 A1) discloses a PEMS microcantilever device that may be used to detect biopolymers in solution Kim discloses a low-cost device that is portable. Kim et al. discloses forming several cantilevers on one substrate so that one cantilever may be used for frequency measurement and the others for measuring a sensing frequency. This method allows the detection of multiple materials simultaneously in a solution. Kim et al. fails to disclose how antibodies are attached to the PEMS microcantilever. While Kim et al. detects multiple biopolymers using one detection system, the testing surface attaches antibodies to a Cr and Au deposited surface via calixcrown SAM thereof. Calixcrown SAM only works for proteins of at least 20,000 Daltons (20 kDa) that include an ammonium ion. This method would not work for DNA or RNA because both DNA and RNA lack ammonium ions, and this method could not be used with proteins lacking ammonium ion (which will be rare in normal blood pH).

Human blood comprises ions, gases, proteins, platelets, red blood cells, white blood cells, DNA, RNA, viruses, antigens, antibodies, hormones, and other components. In the past, microcantilever probes have been ineffective and unreliable in detecting viral infection or disease progression due to their lack of specific binding. Microcantilever probes are composed of silicon compounds. Silicon compounds are non-reactive with biological agents. The microcantilever surface must be modified in order to permit binding of biological compounds. Additionally, the surface must be modified so that non-specific biological compounds will not to the modified cantilever surface. Antibodies with specific binding to certain antigens have been developed. But, the antibodies have been bound via amine bonds, which are unstable in complex solutions such as a blood sample. And, the antibodies bind via amine bonds in a non-specific manner such that an amine bond may be formed between the cantilever surface and an amino acid on the active site blocking antibody-antigen binding. Additionally, the antibody must be bound and maintained under neutral pH to prevent changes in conformation, which may cause changes in the active site of the antibody binding area causing a reduction or increase in antibody binding affinity ability with the correct antigen. In order to be reliable, the binding agents attached to the PEMS surface must be strongly bonded and unlike to disassociate, the structural integrity of the binding agent must be maintained so that the active site of the binding agent is accessible, and the conformation of the binding agent must be maintained. Additionally, a test that allows for microcantilever detection of nucleic acid is needed to ensure diagnosis prior to the production of antibodies. Also, a test that allows the quick screening for genetic mutations/variants is needed to enhance diagnosis and treatment of cancer.

DETAILED DESCRIPTION OF THE INVENTION

Figure 1:
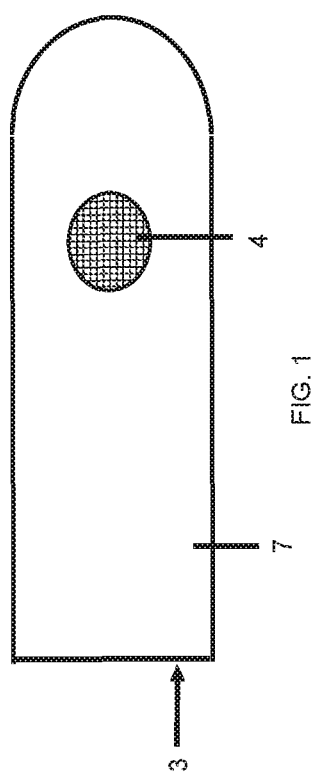
FIG. 1 depicts an exterior top view of a detachable test sensor head 7.

While this invention is susceptible of embodiment in many different forms, there are shown in the drawings and will herein be described in detail, several embodiments with the understanding that the present disclosure should be considered as an exemplification of the principles of the invention and is not intended to limit the invention to the embodiments so illustrated. Further, to the extent that any numerical values or other specifics of materials, et., are provided herein, they are to be construed as exemplifications of the inventions herein, and the inventions are not to be considered as limited thereto.

The following description and drawings are illustrative and are not to be construed as limiting. Numerous specific details are described to provide a thorough understanding of the disclosure. However, in certain instances, well-known or conventional details are not described in order to avoid obscuring the description. References to one, or an, embodiment in the present disclosure can be, but not necessarily are, references to the same embodiment; and, such references mean at least one of the embodiments.

Reference in this specification to "one embodiment' or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments, but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same term can be said in more than one way.

Consequently, alternative language and synonyms may be used for any one or more of the terms discussed herein, or is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the disclosure or of any exemplified term. Likewise, the disclosure is not limited to various embodiments given in this specification.

Unless otherwise defined, all technical and scientific terms used herein have the same meaning as commonly understood by one of ordinary skill in the art to which this disclosure pertains. In the case of conflict, the present document, including definitions will control.

A "cantilever probe" includes any piezoelectric sensor that is both a micro-electrical and a micro-mechanical sensor that is able to detect micro changes in both electrical and mechanical properties upon binding. PEMS utilizes a piezoelectric layer to enhance detection of the micro-electrical changes resulting from changes in resonance or resistance in the micro-mechanical sensor. Binding occurs on a surface of the PEMS micocantilever probe, which causes the mechanical bending of the PEMS micocantilever probe. A "converter" converts a digital signal produced from the mechanical bending of the microcantilever upon binding to a substrate into a readable language. Cantilever, microcantilever, and PEMS are interchangeable in this disclosure.

A "surface modification agent" is an agent, chemical compound, chemical process, or the combination of agents that is may be used to modify the surface of a cantilever probe in order to make said cantilever probe more receptive to binding on its surface, which facilitates a change in resonance in the cantilever probe that may be detected as disclosed in the prior art.

A "linker" is a compound or substance applied to a portion of the cantilever probe surface that allows the attachment of one or more "binding agents". A "binding agent" is a substance that physically binds to both the linker and with a targeted biological compound that indicates a specific viral infection or a cellular mutation in a patient's aqueous sample. If the biological compound indicates HIV infection it is a "HIV component". If the biological compound indicates Ebola infection or Hepatitus C infection it is a "Ebola component" or "HCV component", respectively. If the biological compound indicates a cancer or genetic mutation it is a "cancer component". "Binding agents" are biological compounds, such as antibodies, RNA or DNA, that specifically bind HIV components, Ebola components, HCV components, or cancer components to the microcantilever sensor. "HIV component" includes, but is not limited to antibodies to: gp41, gp120, tat protein, gag protein, p24, p17, HIV, and certain DNA and RNA sequences associated with HIV-1 and HIV-2. "Ebola component" includes, but is not limited to, an antibody to Ebola virons, Ebola RNA, Ebola DNA, or other substance associated with Ebola infection. "HCV component" includes, but is not limited to, an antibody to HCV virons, HCV RNA sequence, HCV DNA sequence, or other biological compound associated with HCV infection. "Cancer component" may include antibodies to specific cancer, DNA and/or RNA sequences associated with a specific cancer or cancer mutation.

Embodiments of the present invention may include one or more of the following features.

"PEMS cantilever", "PEMS microcantilever" "cantilever", and "microcantilever" are used interchangeably herein. Cantilever arrays allow real-time detection and analysis of chemical agents. Cantilever sensors are relatively cheap and allow testing of very small sample volumes. Cantilevers are piezo microelectromechanical sensors (PEMS) that convert micro mechanical resistance into an electrical signal. Cantilevers are formed of silicon (Si), silicon nitride ($Si_3N_4$), or a polymer. Cantilevers are formed of multiple layers of silicon wafers (masks) with piezoresistive integrated resistor CMOS technology. The multiple layers are annealed to assemble the silicon mask and bridge. Cantilevers are coated with a piezoelectric thin film for self-actuating and sensing purposes. A piezoelectric film may be deposited on at least one side of an upper surface and a lower surface of the cantilever. A lower electrode formed at a lower surface of the piezoelectric film, an upper electrode formed at an upper surface of the piezoelectric film, and an electric pad that supplies electric current to both the lower electrode and the upper electrode. The cantilever is typically longer than it is wide, and includes, but is not limited to, a rectangular shape, a "U" shape, a "V" shape, or a rectangle with a square on the end (the square end interacts with the analyte). Single cantilevers may be formed of various lengths, widths, and thicknesses. A typical cantilever may be 50 microns long, 1 micron wide, and 500 nm thick. The cantilever is fixed at one end and moves at the opposite end when it interacts with an analyte. A number of cantilever sensors may be assembled into an array. For example, an exemplary sensor array may be comprised of one hundred individual cantilever test sensors.

A number of cantilevers may be arrayed so that a single cantilever reference sensor is paired with a single cantilever testing sensor. Alternatively, multiple cantilever test sensors may be paired to a single microcantilever reference sensor. The cantilever array my be maintained in solution and the analyte being tested may be contained within a liquid volume. Alternatively, the test sensor may be dried and stored until later use.

While micro cantilevers shown in the figures herein are depicted as having a single surface level, cantilevers with micro-cavities on the binding surface may be used. If cantilevers with micro-cavities are used, then micro printing technology may be employed to deposit binding agents.

FIG. 1 depicts an exterior, top view of the detachable test sensor head 7. The device may be self-contained and include a detachable sensor head 7 that attaches to a body at connection line 3 wherein the body includes the electrical and mechanical components that convert the change in resonance or resistance within the PEMS microcantilever test sensor into a detectable and quantifiable digital signal. The exterior body of sensor head 7 may be hollow and composed of plastic. The PEMS microcantilever sensor(s) is contained within well 4 and bathed in buffer solution. Alternatively, well 4 may be left without buffer. Binding agents such as IgG, RNA, and DNA are highly stable if rinsed in deionized water and air dried. The device may be stored without buffer and the device used to test a liquid sample without the addition of buffer. PEMS cantilevers that have been functionalized are highly stable and may be stored indefinitely if dried and stored properly.

Figure 2:
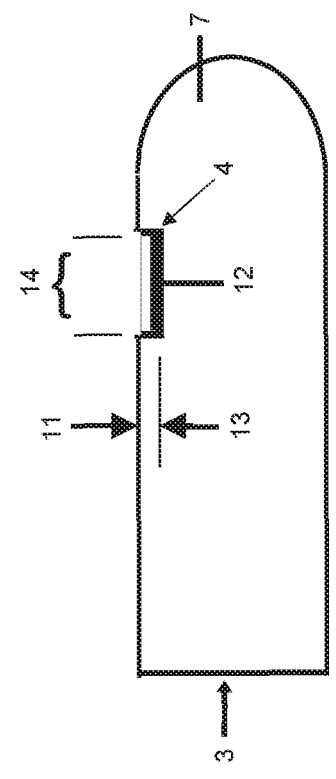
FIG. 2 depicts an exterior, side view of the detachable test sensor head 7 with the cover detached.

FIG. 2 illustrates an external, side view of a detachable test sensor head 7. The PEMS microcantilever device herein may be positioned within a portable device, such as that shown in Kim et al. (US 2005/0112621 A1), or positioned within a non-portable, fixed device in a laboratory setting. This device relates to the functionalization of the PEMS microcantilever sensor and not to the structure of PEMS detection devices. A PEMS microcantilever processing means is necessary to capture data from the cantilever sensor and to process the captured data. Detachable test sensor head 7 contains the cantilever sensor(s). Connector line 3 is a proposed connection point for connect detachable test sensor head 7 to a processing means (not shown). If a detachable test sensor head 7 is utilized, then one processing means may be used multiple times to capture and process data by simply detaching a used detachable test sensor head 7 and replacing it with a new, unused detachable test sensor head 7. This reduces waste and costs. Alternately, the probe may be a one-time use probe. Detachable test sensor head 7 may include test well 4, which is shown enclosed by cover 6. Cover 6 covers test well 4 and may be retracted or removed to allow a sample to be added to the well 4. Cover 6 protects the microcantilever sensor(s) from contamination and seals in buffer solution (if used) to prevent leakage of said buffer solution. Test well 4 may contain buffer solution, such as HEPES, and the cantilever sensor. Test well 4 contains sufficient buffer solution to fully bathe the cantilever sensor(s).

Test well floor 12 has diameter 14. The depth of test well 4 is that distance between the surface 11 the detachable test sensor head 7 and Line 13, which is a line extending out from test well floor 12. The total volume contained within test well 4 is Volume Total. The amount of buffer, or Buffer Total, contained within test well 4 is Volume Total minus the volume of a single blood drop, or Sample Volume. Volume Total equals Buffer Total plus Sample Volume. This allows a sample to be collected by pricking a finger, and then squeezing a single blood drop into test well 4. Test well 4 is designed so that any excess blood sample would spill over the edges of surface 11, allowing the concentration of blood to be accurately determined. This feature allows viral concentration, or viral load, to be quantified for HIV, HCV, Ebola, or other viruses.

Individual cantilever sensors have an extremely small mass, which results in each cantilever having an extremely small resistance capacity. Piezo materials are excellent conductors of electrical voltage. The addition of piezo materials allows binding of biomolecules to be detected by measuring changes in shift in resonance frequency of the cantilever using an atomic force microscope ("AFM"). AFM are expensive and can be difficult to use. Piezoresistive materials allow monitoring of the cantilever sensor by measuring changes in deflection or resistance of the cantilever or the piezo material when the cantilever deforms. The change in deflection/resistance can be measured by measuring the output voltage of the system. However, there is difficulty in fabricating the sensor with the embedded resistor. The application of small excitation voltages to the PEMS microcantilever sensor creates small, but quantifiable, changes in deflection/resistance. A cantilever sensor without bound viral or cancer components will have a certain deflection or resistance voltage output. Upon binding of either viral or cancer components, the deflection and resistance of the cantilever sensor will change. This change can be monitored and quantified by monitoring the change in voltage output of the cantilever.

Antibodies are typically large, complex biological molecules comprised of a large number of amino acids that selectively bind to antigens. Antibodies can be produced so that they will bind to a large variety of proteins, bacteria, viruses, foreign substances in blood, and to a number of other organic compounds. A number of antibodies are known in the art, such as PSA (prostate specific antibody), and antibodies utilized in ELISA to detect HIV (outlined above), cancer, and certain diseases. A number of antibodies have been bound to PEMS and MEMS microcantilevers. All previous applications have utilized methods of binding antibodies to the cantilever surface via an amine bond. Amine bonds are fairly week. In a complex aqueous solution, antibodies adhered or linked to the cantilever surface may disassociate, causing other amine bonds to form on the cantilever surface. Additionally, the current methods do not prevent unspecific amine bonds from forming, which allows amine bonds to form between the cantilever surface and amine functional groups on undesirable locations on the antibody, such as locations in the antibody active site or locations that block antibody-antigen bonding.

HIV-1 is a single-stranded RNA virus that is detectable in peripheral blood in just eleven days after initial infection. HIV-1 RNA levels in plasma indicate viral load. A single strand of RNA attached to the PEMS microcantilever surface may be used to bind with a complimentary single strand of HIV RNA, HCV, Ebola, oncolytic virus, or other viral RNA. The RNA bound to the cantilever surface preferably binds with a complimentary single strand of RNA of 61 nucleotides in length. Several conserved secondary structure elements have been identified within the HIV RNA genome. The 5'UTR structure consists of series of stem-loop structures connected by small linkers. These stem-loops (5' to 3') include the trans-activation region (TAR) element, the 5' polyadenylation signal [poly(A)], the PBS, the DIS, the major SD and the hairpin structure located within the 5' end of the genome and the HIV Rev response element (RRE) within the env gene. Another RNA structure that has been identified is gag stem loop 3 (GSL3), thought to be involved in viral packaging. Each of these stem-loops are composed of single stranded RNA. A single strand of RNA that is complimentary to at least one of these stem-loop regions may be attached to the PEMS surface allowing the HIV RNA (which is 9749 nucleotides long and has a weight of 3,124 kDa) to bind to the PEMS surface creating a change in voltage across the cantilever sensor.

HCV (hepatitis C virus) RNA is detectable in blood in just one week after infection, while HCV antibodies are present in 6 to 8 weeks post infection. HCV RNA in plasma is both single and double stranded. The current method of detecting HCV RNA includes PCR (polymerase chain reaction). In order to perform PCR, a blood sample is drawn, preservatives added to the sample, and the sample is transported to a lab for analysis. The addition of preservatives and time expended in transport and processing effect the accuracy of the test. Hepatitis C virus is a single stranded RNA virus of 16.8 kDa in mass. The invention herein allows a single strand of HCV RNA to be adhered to the PEMS cantilever surface. Upon the addition of a drop, or larger sample, the PEMS cantilever is able to detect binding with HCV RNA suggesting viral infection of the tested sample. The efficacy of the test may be enhanced by adding Triton X-100 to test well 4 prior to testing. HCV RNA may be encapsulated so that viral RNA is not accessible to the cantilever sensor. Triton X-100 (which is a mild detergent with a pH of 6.0 to 8.0) breaks up HCV viral capsid causing the RNA to be released so that the presence of HCV RNA may be accurately tested.

A single strand of DNA bound to the PEMS microcantilever surface may be used as a binding agent to bind with a complimentary strand of cancer DNA. For example, a single strand of DNA of just 65 nucleotides has a mass of 20 kDa (20 kilodaltons or 20,000 Daltons). This device can detect and quantify a change in binding of a single strand of DNA of 66 nucleotides. This device is highly sensitive to the binding of a small single strand of DNA. ctDNA (circulating tumor DNA) is released by tumor cells and circulates in the blood where it harbors the mutations of the original tumor. Tumor cells and lymphocytes continuously and automatically release DNA into plasma. ctDNA may be single or double-stranded DNA and may include DNA associated with oncolytic viruses. ctDNA may be comprised of small DNA fragments and has been found to have an approximate length of 160 bases, or 48.67 kDa, which is large enough to allow detection at a single binding site on a PEMS sensor. Single-stranded ctDNA may be detected by the invention herein. For example, single-stranded DNA complimentary to HPV, an oncolytic virus that causes cervical cancer in women, may be linked to the PEMS surface. This single-stranded DNA complimentary to HPV will bind to single-stranded HPV ctDNA causing a change in deflection and resistance that can be detected by detecting voltage through the cantilever sensor.

Figure 3:
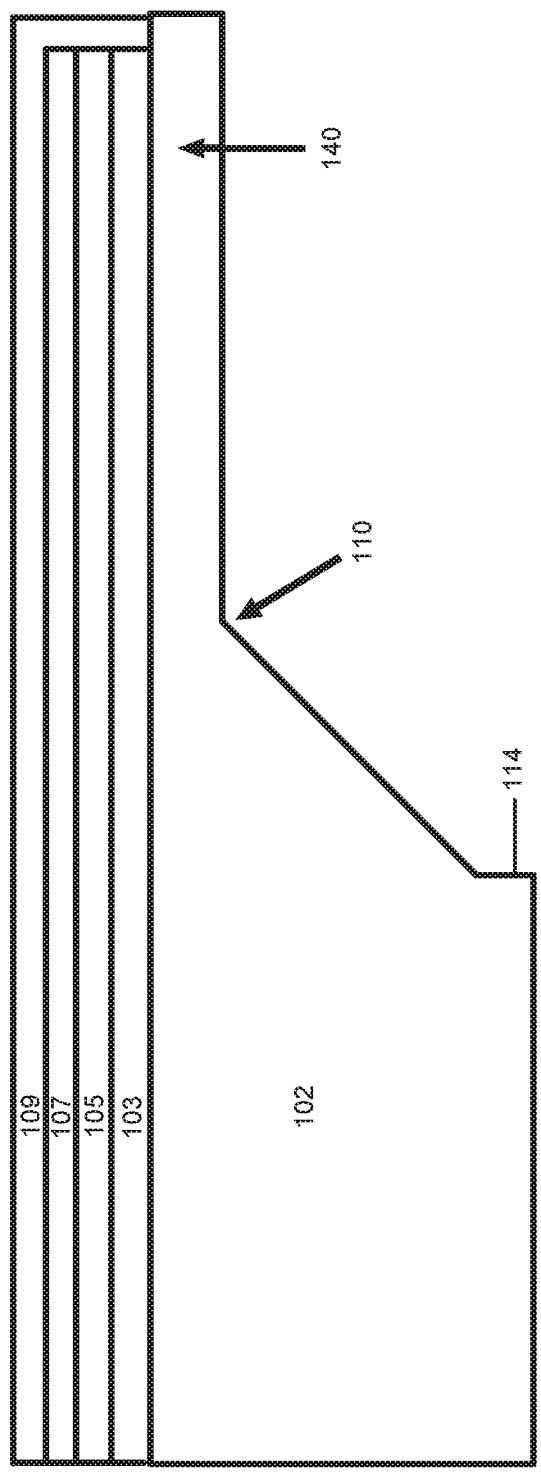
FIG. 3 depicts a single cantilever reference sensor 102 that is housed within the test well of the detachable body.

FIG. 3 illustrates cantilever reference sensor 102, which is a piezoelectric capacitor for self-sensing and actuating on at least one side of the sensor. Cantilever reference sensor 102 includes a piezoelectric film that may serve as a PEMS reference sensor. Cantilever reference sensor 102 is formed using the PEMS method wherein the layers are formed by repeated deposition and etching on the sensor. PEMS cantilever reference sensor 102 may be functionalized with binding agent in order to be used to detect biological components in aqueous solution. Cantilever reference sensor 102 includes base 114, hinge 110, which is a Wheatstone bridge, and beam 140, which is the free end. Hinge 110 comprises the fixed end of cantilever reference sensor 102. The cantilever reference sensor 102 is composed of silicon wafers, also known as silicon "masks", with piezoresistive integrated resistor ("CMOS") technology integrated within. Silicon ("Si") wafers may be composed of silicon dioxide ($SiO_2$) or silicon ("Si") and nitrogen ("N") (silicon nitride $Si_3N_4$) for PZT-thin film based PEMS. The silicon nitride surface of the cantilever reference sensor is non-porous and uncharged, and therefore, does not bind or absorb biomolecules. Alternatively, the cantilever reference sensor 102 may be fabricated from Cu, Sn, Ni, Ti, or any combination thereof. Cantilever sensor reference 102 may be of any thickness or length, and be of any shape, such as rectangular, triangular, circular, elliptical, or any other geometric shape.

While cantilever reference sensor 102 requires only cleaning prior to use, the surface of beam 140 of must be modified so that it can bind/interact with biological components.

The piezoelectric layer(s) may be constructed from any piezoelectric material, preferably highly piezoelectric materials, such as lead magnesium niobate-lead titanate (Pb$(Mg_{1/3}Nb_{2/3})O_3)_{1-x}$—$(PbTiO_3)_x$ (PMN1x-PT$_x$) films (PMN-PT), where $0.3<x<0.4$, highly piezoelectric lead zirconate titanate (PZT) films and sodium potassium niobate-lithium niobate solid solutions (NKN-LN). In an exemplary embodiment, the piezoelectric layer may be fabricated from any highly piezoelectric material with a high $-d_{31}$ coefficient of about 20 pm/V$<-d_{31}<$5000 pm/V, preferably about 200 pm/V$<-d_{31}<$5000 pm/V.

Piezoelectric film 105 is stacked on top of lower electrode 103 surface. Upper electrode 107 stacks on top of the surface of piezoelectric film 105. Lower electrode 103, piezoelectric film 105, and upper electrode 107 are utilized to capture changes in deflection and resistance in cantilever beam 140 during testing. Piezoelectric film 105 enables the detection of small changes in the mV range to be detected by the device. Piezoelectric film 105 may be any compatible piezoelectric material. Insulation film 109 covers the surface of upper electrode 107 and the thickness of upper electrode 107, piezoelectric film 105, and lower electrode 103. Insulation film 109 may be any suitable material to prevent electrical conduction within the blood or aqueous sample being tested. Insulation film 109 may be an inorganic material such as SiOx or an organic material such as parylene. The upper electrode 107 and lower electrode 103 are connected to a electric pad (not shown) that converts the mechanical change at beam 140 into an electrical change that can be quantified. The probe may be configured so that voltage changes in either the cantilever sensor or the piezoelectric material may be detected.

Figure 4:
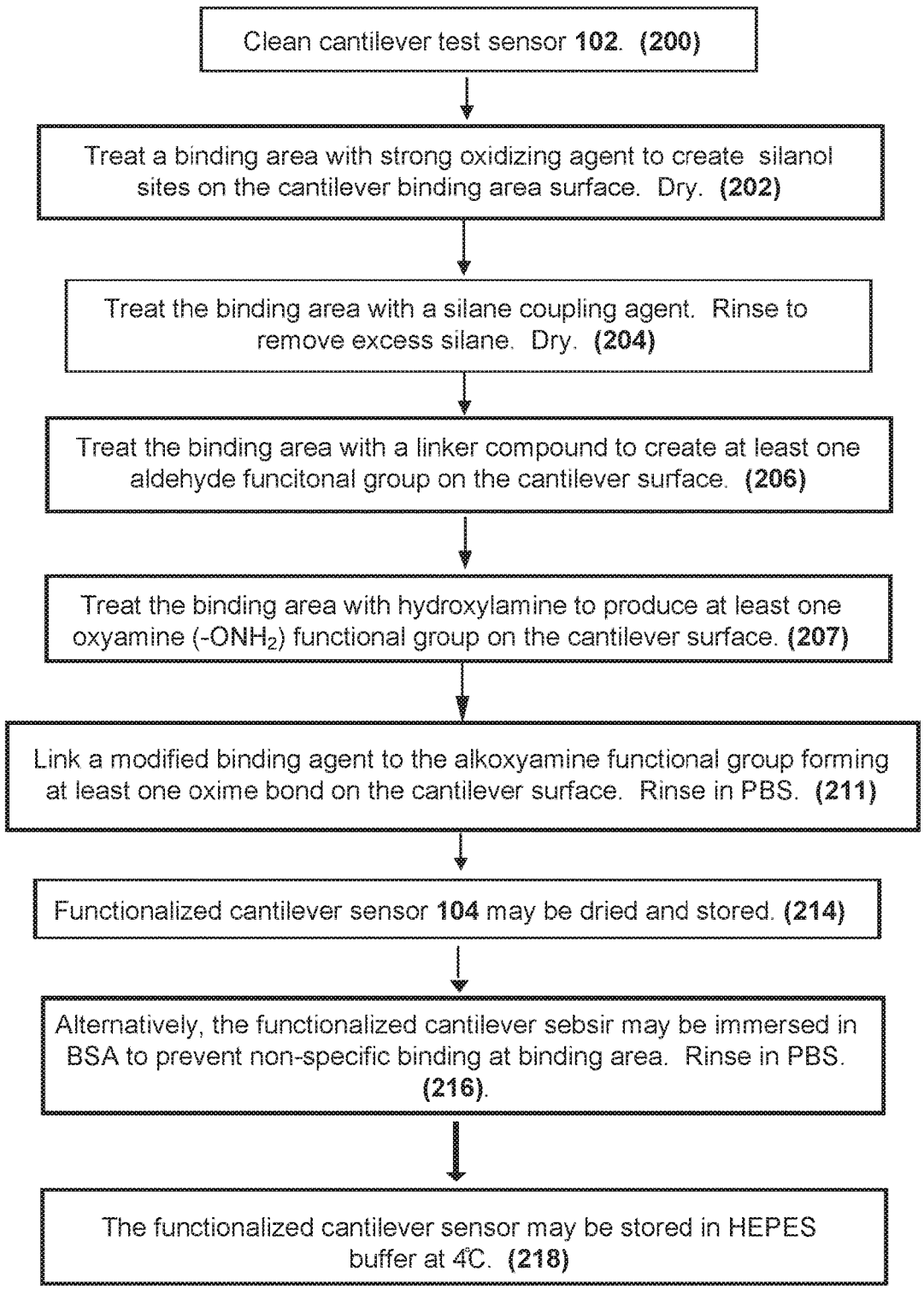
FIG. 4 is a flow chart depicting the method of modifying the cantilever reference sensor 102 so that it is a functionalized PEMS microcantilever test sensor 104 utilizing a oxime bond.
Figure 5:
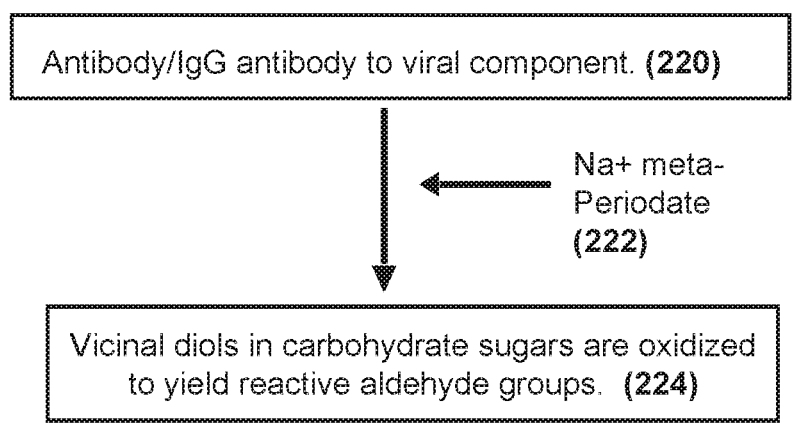
FIG. 5 is a flow chart depicting the preparation of antibody/IgG binding agents so that they can be bound to the microcantilever sensor.
Figure 13:
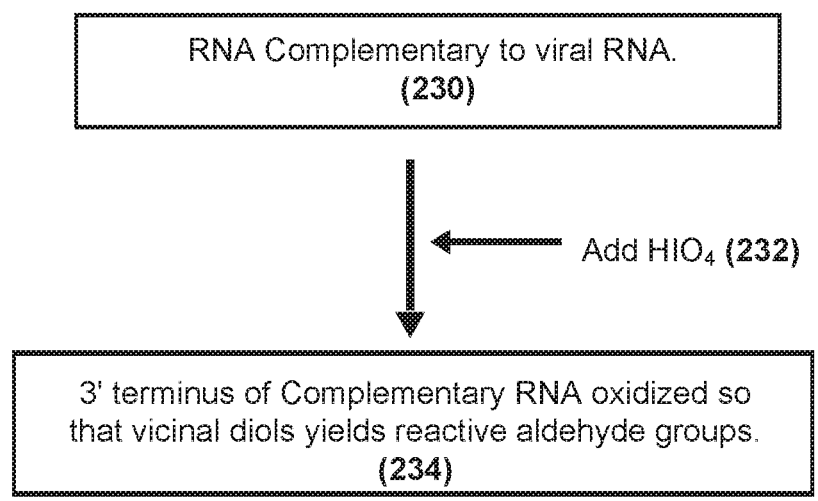
FIG. 13 is a flow chart depicting the modification of RNA prior to binding to PEMS microcantilever test surface.
Figure 16:
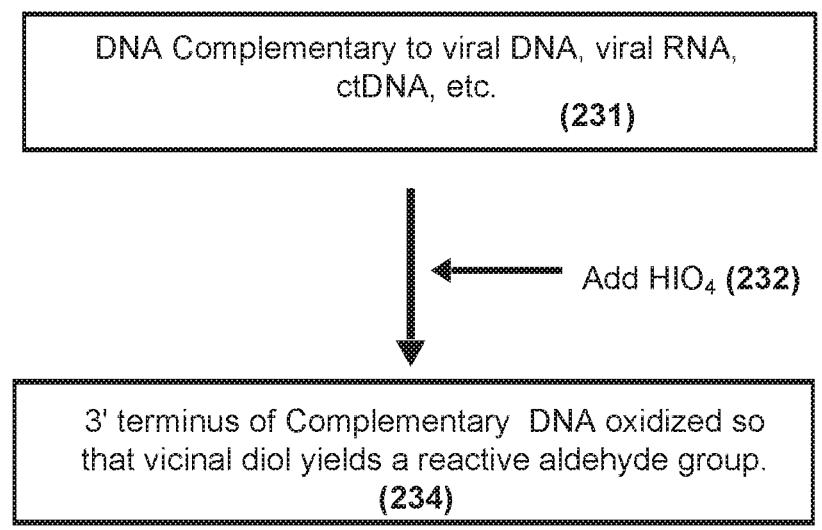
FIG. 16 is a flow chart depicting the modification of DNA at step 232.

FIG. 4 is a flow chart depicting a process of functionalizing cantilever test sensors. The method of preparation of the PEMS cantilever surface is the same whether IgG, DNA, or RNA is used as a binding agent. This method requires modification of the binding agent prior to its attachment to the PEMS surface. FIGS. 5, 13 and 16 are flow charts depicting the modification of binding agents, such as antibody immunoglobulin ("IgG"), RNA, and DNA, respectively, prior to their attachment to cantilever test sensor 102.

This method creates a chemical linkage between the PEMS microcantilever surface and the binding agent. This method does not use an amine bond as the chemical linkage because amine bonds are weak and hydrolyze in aqueous solution at neutral pH. At neutral pH, amine bonds in aqueous solution hydrolyze freely which may reverse the chemical link between the binding agent and the cantilever surface causing the binding agent to be released from the cantilever surface reducing or eliminating the ability of the cantilever to bind with binding components.

The prior art discloses binding biological molecules to a sensor via an amine bond wherein a nitrogen on the biomolecule binds with a carbon on the sensor. Nucleic acids do not have exposed or available carbon atoms to form an amine bond. Nucleic acids have non-reactive ribose sugars on their reactive 3' termini. Ribose sugars do not generally form amine bonds with other compounds.

This method utilizes either an oxime bond or a hydrazone bond as the chemical linkage between the PEMS microcantilever surface and the binding agent. Both oxime and hydrazone bonds are relatively stable in aqueous solution at neutral pH. Oxime and hydrazone bonds will form with both antibodies, or IgG, and nucleic acids that have been modified to include at least one aldehyde moiety.

Oxime bonds are more stable in aqueous solution than hydrazone bonds. If the cantilever sensor is to be maintained in solution during distribution and storage, then a user may utilize the oxime bond method depicted in FIG. 4. If the cantilever sensor is to be dried before distribution and storage, then the user may utilize either the oxime bond method depicted in FIG. 4 or the hydrazone method depicted in FIG. 8. Both the oxime and hydrazone methods allow drying of the completed sensor when utilizing nucleic acid as a binding agent. Dried oximes and dried hydrazones are highly stable during storage and distribution.

FIG. 4 depicts the functionalization of PEMS cantilevers with a oxime bond. Antibodies, RNA, and DNA may be bound to the PEMS cantilever via an oxime bond. Functionalization may begin with the cleaning of PEMS microcantilever sensors at step 200. Cantilever sensors 102 may be cleaned by soaking in deionized water, subjecting them to ultraviolet light and ozone for 15 minutes, or rinsing/sonicating them with phosphate buffer solution ("PBS").

Additionally, cantilever sensors may be cleaned by washing in a alternating solutions of 70% ethanol/10% HCl, ultrapure water, and/or 100% ethanol. Any other suitable method that frees all exterior surfaces of the silicon wafers of contaminants may be utilized.

At step 202, active binding area 330 of cantilever test sensor 104 is treated with a surface modification agent, such as an oxidizing agent. Binding area 330 may be positioned on the bottom surface of beam 140 to reduce interference from non-binding components within the aqueous sample. Sulphochromic acid is an exemplary surface modification agent. Sulphochromic acid may be applied the binding area 330 of cantilever test sensor 102 for 10 minutes. Another oxidizing agent is Piranha (30% $H_2SO_4$ conc. in $H_2O_2$, 1:1), which may be applied to binding area 330 for twenty minutes. The oxidizing agent creates silanol sites on the $Si_3N_4$ surface of the bottom surface of beam 140. The silanol surfaces allow organic compounds to be coupled to the inorganic silicon surface. Next, PEMS cantilever test sensors 102 may be dried by heating under vacuum following application of the oxidizing agent.

Cantilever active binding area 330 can be any length and width on the surface of beam 140. Locating binding area 330 on the bottom surface of beam 140 causes the weight of bound IgG, DNA, and/or RNA to move beam 140 about hinge 110 relative to base 114 (shown in FIGS. 23, 25, and 27).

Micro-cavity cantilevers may be used so that the bottom surface of beam 140 includes multiple small functional areas. This will allow a single micro cantilever to have multiple binding areas within a single cantilever. A single cantilever may be micro printed with two or more binding sites for the same binding agent increasing the effectiveness of the cantilever reference sensor in dilute solution. Instead, a single PEMS cantilever may be micro printed with two or more binding sites so that two different binding agents allowing a single sensor to be responsive to two different binding components. This allows a single cantilever to test for both HIV p24 antibody and HIV protease antibody simultaneously. A micro cantilever with micro-cavities reduces the total number of cantilevers needed in a given embodiment, thus, reducing the overall costs of the assay. Additionally, functionalizing only micro-cavities means that step 214 (application of BSA) does not have to be included in the process because only the micro-cavities are functionalized and binding components will not adhere to the silicon surface of the cantilever beam 140 surface.

Figure 20:
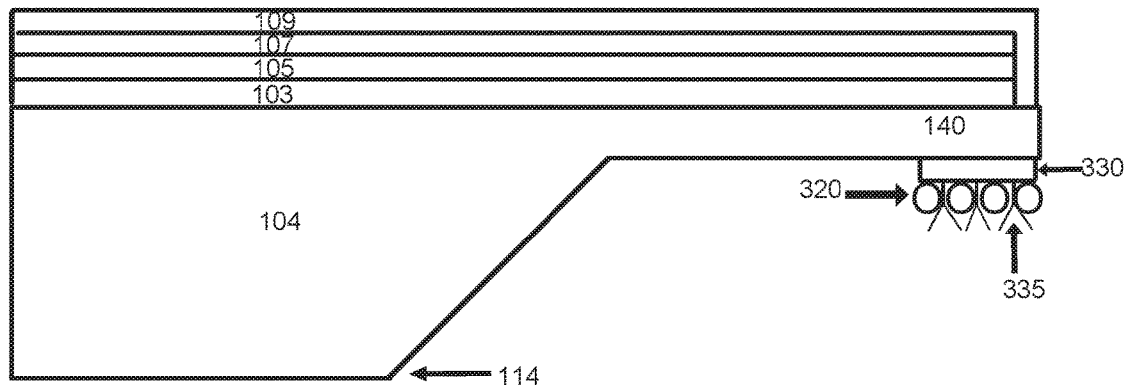
FIG. 20 illustrates the fully functionalized PEMS microcantilever test sensor produced at FIG. 4.

FIG. 20 depicts binding area 330 covering the bottom surface area of beam 140 toward the outer tip of beam 140. Binding area 330 may be positioned along the top or bottom of beam 140 in any desired location, or in multiple locations along beam 140. The larger binding area 330 utilized, the larger number of potential binding sites for binding components 350.

Next, at step 204, binding area 330 is treated with a silane coupling agent. For example, binding area 330 of cantilever test sensor 102 may be treated with 1% silane (N-[3-(Trimethoxy-sily)Propyl-Ethelene Diamine, 97%) is an exemplary silane coupling agent. The cantilever sensor may be subjected to treatment with 1% silane (N-[3-(Trimethoxy-sily)Propyl-Ethelene Diamine, 97%) for five minutes, rinsed in ethanol to remove excess silane, and dried by heating the samples at 110° C. for 10 minutes in argon ambient. The silane coupling agent binds to the silicon nitride surface forming an organic coating layer enhancing adhesion of linker compounds. Alternate silane coupling agents that may be utilized include (3-Aminopropyl) triethoxysilane and 3-(glycidyloxypropyl)dimethylethoxysilane. Step 204 creates a primary amine surface on binding area 330.

The primary amine residue created at step 204 will non-selectively bond with binding agents 335 including bonding with residues on the active site of the antibody reducing or eliminating the ability of the antibody to bond with HIV components 350. And, any bonds formed between the primary amine surface created at step 204 and an antibody will be weak and likely to disassociate randomly. Also, the chemical reaction wherein the primary amine surface bonds with the antibody has a high activation energy and is disfavored with a low rate of efficiency. The addition of an enzyme to reduce the activation energy will alter the ability of the antibody to bond with HIV components 350.

At step 206, the binding area 330 is treated with a linker compound to create aldehyde sites on the water surface. Gluteraldehyde may be utilized as a linker compound to create aldehyde moieties on the cantilever surface of binding area 330. The cantilever sensor may be subjected to 1% aqueous glutaraldehyde, which is a homo-bifunctional agent, for 30 minutes. Gluteraldehyde treatment creates free aldehydes on the surface of binding area 330. These aldehydes can then be used as a linker to bind binding agents 335, or can be modified further prior to binding of binding agents 335. It's the addition of the aldehydes on the surface of binding area 330 that allow the use of the cantilever to detect biomolecules.

An aldehyde will react with any amine functional group of an antibody, or IgG binding agent 335. The amine bond is formed between the carbon of the aldehyde group of the surface of binding area 330 and the nitrogen of an IgG binding agent 335. This amine bond is weak and may disassociate in complex aqueous solution, such as a blood sample. Any disassociation of bound binding agent 335 from binding area 330 creates an area wherein other compounds within the aqueous solution may bind to the aldehyde site on binding area 330, which destroys the reliability of the PEMS microcantilever sensor. This lack of reliability prevents the use of prior art devices as a sensor in medical applications. Also, the disassociation of bound binding agent 335 reduces the number of binding sites with functional antibody or IgG binding. Any reduction in viable binding sites reduces the effective binding capacity of the microcantilever sensor, precluding the use of the assay for determination of viral load. Additionally, the loss of active binding sites on the surface of binding area 330 reduces the ability of the cantilever sensor to detect small quantities of binding component 350. Each disassociation of binding agent 335 is not only the loss of a test site, but also injects into test well 4 unbound binding agents 335 that may freely and irreversibly bind to antigen, HIV virons, p24, Ebola virons, etc, within the sample being tested. The disassociation of binding agent 335 reduces the number of binding component 350 in solution that are free to interact and bind with binding agent 335, which reduces the ability of the sensor to detect the presence of viral components or cancer components in the sample being tested. In order to determine the presence of very small quantities of viral binding components or cancer components in a patient's sample allows the detection of infection or disease early in the disease process. Binding agents 335 must be strongly bound to the cantilever sensor in order for the test to be reliable. Additionally, in order to determine viral load, binding agent 335 must be strongly bound to the cantilever surface.

In order to produce a PEMS microcantilever sensor that is both reliable and can detect small quantities accurately, the aldehyde surface created at step 206 must be modified so that a non-amine bond may be formed between the surface of beam 140 at binding area 330 and binding agent 335. The method herein modifies the aldehyde surface of binding area 330 to an oxime bond in order that a strong bond be formed between the surface of binding area 330 and binding agent 335. Oxime bonds are highly stable and unlikely to disassociate at blood pH, even in complex aqueous solutions such as blood.

At step 207, binding area 330 is treated with hydroxylamine to produce the oxyamine (—$ONH_2$) functional group on the surface of binding area 330. At step 211, the oxyamine surface is reacted with vicinal diols in the carbohydrate sugar moieties of modified antibody 224, or IgG, (modification of antibody/IgG is shown in FIG. 5). Step 211 creates an oxime bond wherein the carbon of the modified antibody 224 is double bonded with the nitrogen of the cantilever sensor alkoxyamine surface created at step 207.

The method prevents unwanted amine bond formation because the alkoxyamine surface forms a double bond with the carbon of the modified antibody 224. The double bond of the oxime bond is stable and very unlikely to hydrolyze in aqueous solutions, such as blood, during testing. The oxime bond is highly stable at neutral blood pH, and has been demonstrated to be more stable in aqueous solution than hydrazones.

The method of FIG. 4 may also be used to form oxime bonds between the cantilever surface and modified nucleic acid 234 (shown in FIGS. 13 and 16). Hydroxylamine is an irritant to the respiratory tract, skin, eyes, and other mucous membranes. It may be absorbed through the skin, is harmful if swallowed, and is a possible mutagen. Hydroxylamine may explode when subjected to heat. These negatives translate into additional cost associated with manufacturing.

Upon oxime bond formation at step 211, the cantilever sensor may be rinsed in PBS (phosphate buffer solution), before drying and storage at step 214. Alternatively, the functionalized sensor produced at step 211 may be rinsed in PBS and subjected to BSA (bovine serum albumin) at step 216. BSA binds with any areas of the cantilever sensor binding area 330 that has been modified at steps 202 through 207 but have not formed an oxime bond at 211. This prevents non-specific binding at available aldehyde or oxyamine sites on the cantilever surface. Next, the sensor may be rinsed in PBS and stored in HEPES buffer at step 218. The functionalized sensor may be stored in HEPES for an extended duration to allow for distribution and storage.

FIG. 5 is a flow chart depicting the modification of HIV p24 antibody, HIV protease antibody, IgG, IgM, IgA, or other antibody or immunoglobulin to produce hydrazide binding sites on binding agent 335 that are located away from the active site of the antibody. Any available antibody may be modified pursuant to the method of FIG. 5 in order to be utilized in the method of FIG. 4, or the method disclosed in FIG. 8. Both oxyamine and hydrazide functional groups are reactive with aldehydes (which includes carbonyl groups) and ketones. But, aldehydes and ketones do not naturally occur in antibodies or immunoglobulins. Thus, binding agents 335 lacking aldehydes and/or ketones must be modified so that they will contain aldehyde and/or ketone moieties that will specifically react with the hydrazide surface on beam 140 to form hydrazone bonds on the cantilever surface. This method binds binding agents 335 to the cantilever beam 140 surface via a hydrazone bond. Hydrazide functional groups react well with aldehydes and ketones with a high percent of hydrazone bond formation at neutral pH. It is of critical importance to not introduce binding agent 335 to cantilever beam 140 surface until such time as the pH of the cantilever can be maintained at neutral pH to prevent conformational and other changes to binding agent 335. Any change in pH from neutral pH is likely to cause conformational, protonational and other changes to binding agent 335 that may prevent binding agent 335 from binding to viral components 350 or cancer components 350. This method allows the manufacture and storage of the cantilever sensor 102 in a commercial or manufacturing environment outside of a structural biology or protein lab substantially reducing the costs of production. And, this method allows the cantilever test sensor 102 to be stored in dry, non-aqueous environments for long periods of time at step 210 before the binding of binding agent 335, such as antibody or IgG allowing the device to be maintained for a lengthy period and to be transported and stored without refrigeration.

Antibody, or IgG, at step 220 is subjected to sodium meta-periodate at step 222 for a minimum time, such as 30 minutes, to allow the creation of carbonyl functional groups at step 224 in non-binding areas of the antibody. The carbonyl groups created at step 222 are reacted with both the oxyamine group produced at step 207 and with hydrazide functional groups created at step 212 (shown in FIG. 8).

Immunoglobulin G ("IgG"), or antibodies to viral infection, may be modified as shown include, but are not limited to: gp41, gp120, tat protein, gag protein, p24, p17, HIV, CD4, Ebola IgG, Hepatitus C IgG, etc. HIV p24 antibody and HIV protease antibody are commercially available and may be utilized as an exemplary examples of IgG. IgG is used herein to refer to all antibodies to viral infection. IgG, including antibodies, comprise a "Y" shape with an antigen binding site at the end of each fork at the top of the "Y" (or heavy chains) and two highly conserved N-glycosylation sites below the fork of the "Y" (or light chains). The N-glycosylation sites are composed of carbohydrate or polysaccharides. Modification of the N-glycosylation sites at step 222 by reaction of the binding agent 335 with sodium meta-periodate at step 222 ensures that the antigen binding sites will be unaffected upon binding of the IgG with the hydrazine binding surface 330. At step 220, IgG antibody is selected. A mild oxidizing agent is added to the IgG at step 222. The carbon-carbon bond between the carbohydrates are cleaved between adjacent hydroxyl groups. The concentration of periodate used can be modified for longer length carbohydrate chains. A concentration of 1 mM periodate may be used to ensure that only the ends of the light chains are modified with carbonyl functional groups.

Figure 6:
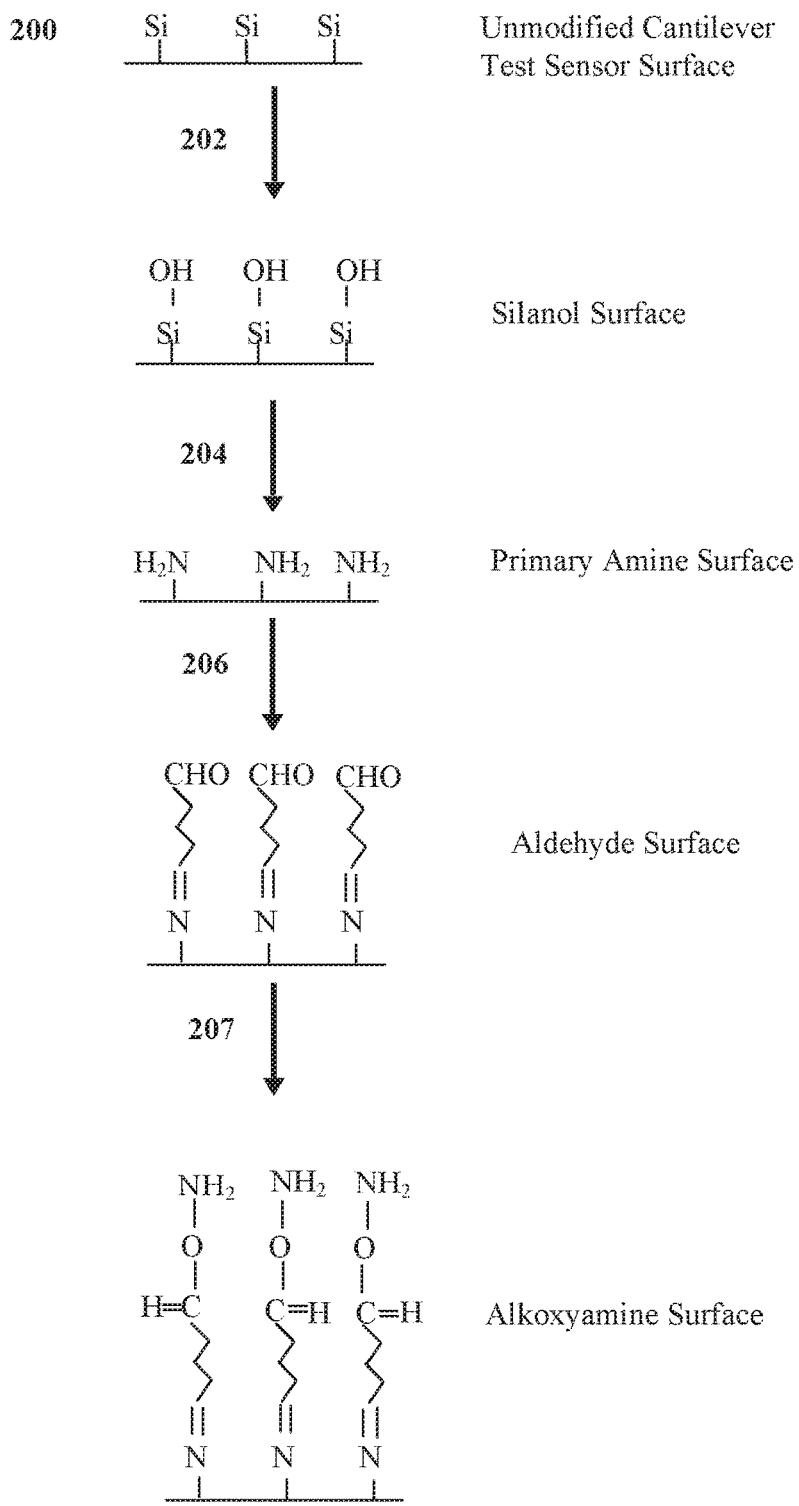
FIG. 6 depicts the modification of the surface of the binding area of the PEMS microcantilever reference sensor 102 using an oxime bond.

FIG. 6 depicts the chemical surface of the cantilever as depicted in FIG. 4. At step 200, the microcantilever test sensor 102 includes Si on the binding area 330 surface. At step 202, the Si surface is modified so that an alcohol (—OH) functional group is coupled onto the Si surface. At step 204, the alcohol moiety is released and a primary amine (—$NH_2$) moiety is bound to the Si surface. The primary amine functional group is reacted with gluteraldehyde to create an aldehyde surface (—CHO). The aldehyde surface is reacted with hydroxylamine to produce the oxyamine surface at step 207.

Figure 7:
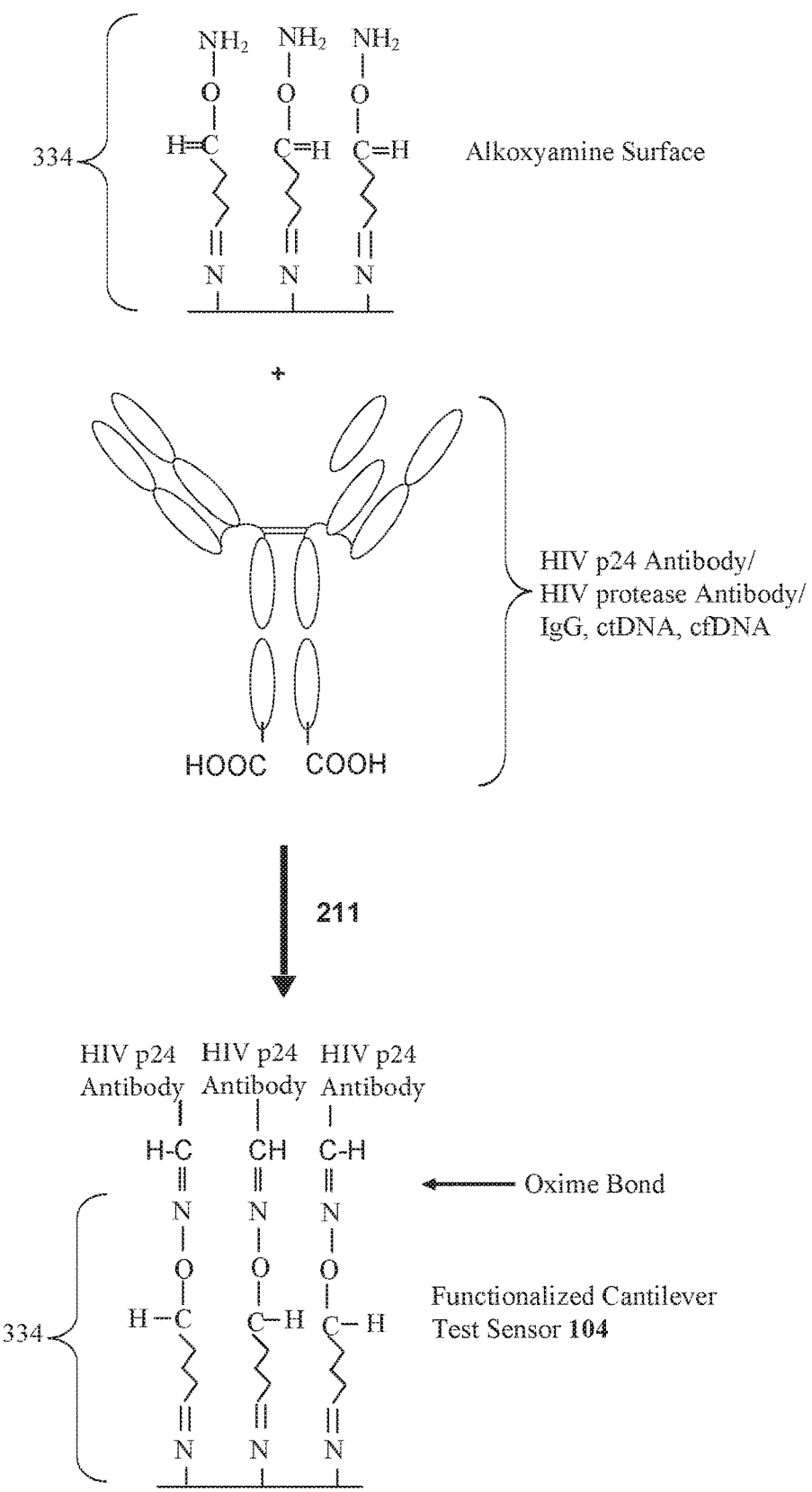
FIG. 7 illustrates step 211 of the method depicted in FIG. 4.

The chemical reaction of the alkoxyamine surface created at step 207 with the modified antibody created at step 222 is shown in FIG. 7. The oxyamine functional group (—$ONH_2$) reacts with the carbon terminus of HIV p24 antibody, HIV protease antibody, or IgG at step 211 to produce the fully functionalized cantilever test sensor 104.

Figure 8:
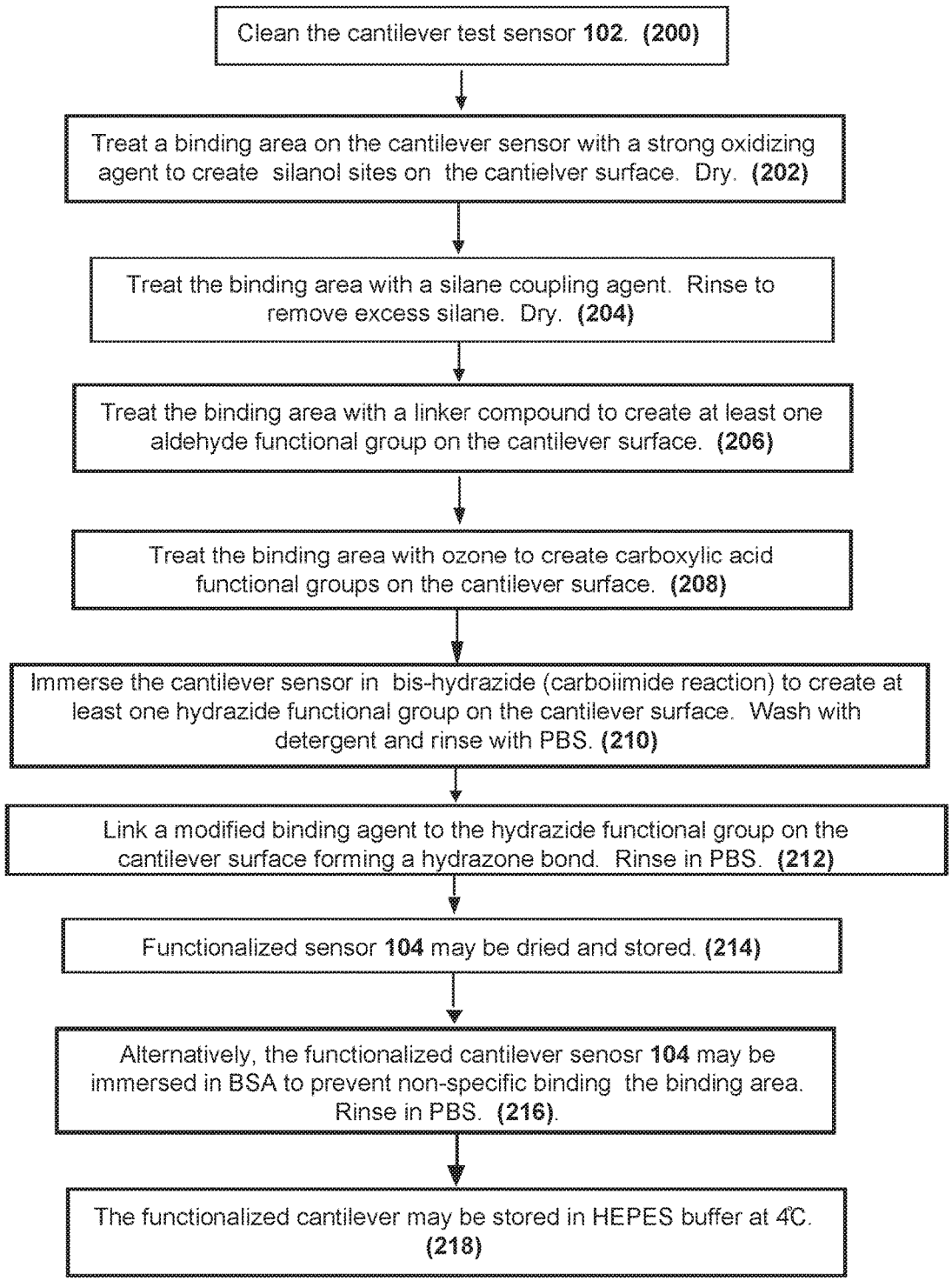
FIG. 8 is a flow chart depicting the method of modifying the cantilever reference sensor 102 so that it is a functionalized PEMS microcantilever test sensor 104 utilizing a hydrazone bond.

FIG. 8 depicts the functionalization of PEMS cantilevers with a hydrazone bond. Functionalization may begin with the cleaning of PEMS microcantilever sensors at step 200. Cantilever sensors 102 may be cleaned by soaking in deionized water, subjecting them to ultraviolet light and ozone for 15 minutes, or rinsing/sonicating them with phosphate buffer solution ("PBS"). Additionally, cantilever sensors may be cleaned by washing in a alternating solutions of 70% ethanol/10% HCl, ultrapure water, and/or 100% ethanol. Any other suitable method that frees all exterior surfaces of the silicon wafers of contaminants may be utilized.

At step 202, active binding area 330 of cantilever test sensor 104 is treated with a surface modification agent, such as an oxidizing agent. Sulphochromic acid is an exemplary surface modification agent. Sulphochromic acid may be applied the binding area 330 of cantilever test sensor 102 for 10 minutes. Instead, Piranha (30% $H_2SO_4$ conc. in $H_2O_2$, 1:1), which may be applied to binding area 330 for twenty minutes. The oxidizing agent creates silanol sites on the $Si_3N_4$ surface of the bottom surface of beam 140. The silanol surfaces allow organic compounds to be coupled to the inorganic silicon surface. Next, PEMS cantilever test sensors 102 may be dried by heating under vacuum following application of the oxidizing agent.

At step 204, the silanol sites are treated with a silane coupling agent. The silane coupling agent creates a primary amine surface on the binding area 330. 1% silane (N-[3-(Trimethoxy-sily)Propyl-Ethelene Diamine, 97%) is an exemplary silane coupling agent. The cantilever sensor may be subjected to treatment with 1% silane (N-[3-(Trimethoxy-sily)Propyl-Ethelene Diamine, 97%) for five minutes, rinsed in ethanol to remove excess silane, and dried by heating the samples at 110° C. for 10 minutes in argon ambient. The silane coupling agent binds to the silicon nitride surface forming an organic coating layer enhancing adhesion of linker compounds. Alternate silane coupling agents that may be utilized include (3-Aminopropyl) triethoxysilane and 3-(glycidyloxypropyl)dimethylethoxysilane.

The primary amine surface created at step 204 will non-selectively bond with residues on the surface of an antibody. These bonds will be non-stable and easily disassociate. There is no means of controlling bonding of the residues created at step 204. Thus, the cantilever surface must be modified further to control bonding binding agent 335 onto binding area 330.

At step 206, the binding area 330 is treated with a linker compound to create aldehyde sites on the water surface. Gluteraldehyde may be utilized as a linker compound to create aldehyde moieties on the cantilever surface of binding area 330. The cantilever sensor may be subjected to 1% aqueous glutaraldehyde, which is a homo-bifunctional agent, for 30 minutes. Gluteraldehyde treatment creates free aldehydes on the surface of binding area 330. These aldehydes can then be used as a linker to bind binding agents 335, or can be modified further prior to binding of binding agents 335. It's the addition of the aldehydes on the surface of binding area 330 that allow the use of the cantilever to detect biomolecules.

An aldehyde will react with any amine functional group of IgG binding agent 335. The amine bond is formed between the carbon of the aldehyde group of the surface of binding area 330 and the nitrogen of an IgG binding agent 335. This amine bond is weak and may disassociate in complex aqueous solution, such as a blood sample. Any disassociation of bound binding agent 335 from binding area 330 creates an area wherein other compounds within the aqueous solution may bind to the aldehyde site on binding area 330, which destroys the reliability of the PEMS microcantilever sensor. This lack of reliability prevents the use of prior art devices as a sensor in medical applications. Also, the disassociation of bound binding agent 335 reduces the number of binding sites with functional IgG binding. Any reduction in viable binding sites reduces the effective binding capacity of the microcantilever sensor, precluding the use of the assay for determination of viral load. Additionally, the loss of active binding sites on the surface of binding area 330 reduces the ability of the cantilever sensor to detect small quantities of binding component 350. Each disassociation of binding agent 335 is not only the loss of a test site, but also injects into test well 4 unbound binding agents 335 that may freely and irreversibly bind to antigen, HIV virons, p24, Ebola virons, etc., within the sample being tested. The disassociation of binding agent 335 reduces the number of binding component 350 in solution that are free to interact and bind with binding agent 335, which reduces the ability of the sensor to detect the presence of viral components or cancer components in the sample being tested. In order to determine the presence of very small quantities of viral binding components or cancer components in a patient's sample allows the detection of infection or disease early in the disease process. Binding agents 335 must be strongly bound to the cantilever sensor in order for the test to be reliable. Additionally, in order to determine viral load, binding agent 335 must be strongly bound to the cantilever surface.

In order to produce a PEMS microcantilever sensor that is both reliable and can detect small quantities accurately, the aldehyde surface created at step 206 must be modified so that a non-amine bond may be formed between the surface of beam 140 at binding area 330 and binding agent 335. The method herein modifies the aldehyde surface of binding area 330 to enable strong bond formation between the surface of binding area 330 and binding agent 335. This is performed herein by the formation of a hydrazide bond on binding area 330 that forms a hydrazone bond when bound with binding agent 335. Both hydrazide and hydrazone bonds are highly stable and unlikely to disassociate at blood pH, even in complex aqueous solutions such as blood.

A hydrazide bond is formed by converting the aldehyde surface at step 206 to a carboxylic acid surface at step 208, and then to a hydrazide surface at step 210. The hydrazide surface can also be utilized to attach nucleic acids such as DNA and RNA (as described later herein).

At step 208, the aldehyde surface of binding area 330 produced in step 206 is treated with ozone to create carboxylic acid functional groups on the surface of PEMS cantilever test sensor 102. At step 210, the cantilever test sensor is immersed in bis-hydrazide (carboiimide reaction) to create a hydrazide surface on the cantilever test sensor 102 surface. Step 210 replaces the carboxylic acid function group produced on the surface of the cantilever at step 208 with the $NHNH_2$ functional group, which is a hydrazide functional group. After the hydrazide functional group is created, the cantilever test sensor 102 may be rinsed first with detergent and second with Phosphate Buffer Solution ("PBS").

The hydrazide functional group formed at step 210 is highly stable and has a reactive amine group that readily reacts with carboxylic acid or other aldehyde functional groups. The hydrazide functional group may form highly stable hydrazone bonds with carboxylic acid or other aldehyde functional groups.

The hydrazide functional group formed at step 210 reacts with aldehyde groups on binding agent 335 to form stable amidine bonds on the surface of binding area 330 at step 212. The hyrdrazide functional group formed at step 210 serves as the cross linking agent that binds the amine reactive group of hydrazide to the aldehyde functional group of binding agent 335 to form a conjugate amidine bond with said binding agent 335. Binding agent 335 is an agent that bonds to hydrazine to form a amidine bond, or an agent that has been modified to do so. Step 212 bonds the binding agent to cantilever test sensor 104 functionalizing it. Cantilever test senor 104 may be washed in detergent, such as Tween, and rinsed with PBS.

At step 214, cantilever test sensor 104 may immersed in bovine serum albumin 320 ("BSA") for IgG applications. Step 214 is not suggested wherein nucleic acid is utilized as binding agents 335. BSA selectively interacts with any areas on the surface of binding area 330 that does not have bound binding agent 335. The surface of binding area 330 was modified at steps 202, 204, 206, 208, and 210 so that it may interact with chemicals and biological agents in a sample being tested. Any areas of the surface of binding area 330 without bound binding agent 335 is subject to unwanted interactions with non-specific molecules in the sample being tested. BSA will interact with the surface of binding area 330 without bound binding agent 335 preventing non-specific binding to cantilever test sensor 104. After BSA binding at step 214, cantilever test sensor 104 should be rinsed (and may be sonicated), and arranged within cantilever test sensor 20 at step 216. The fully functionalized cantilever test sensor 104 may be stored in HEPES buffer at step 218 and stored at 4° C. until used. Alternatively, the fully functionalized cantilever test sensor 104 may be rinsed in PBS with IgG applications and deionized water and air dried for nucleic acid applications. Air-dried RNA, and DNA binding agents are highly stable and may maintain functionality and conformation for a number of years. The air-dried, fully functionalized cantilever test sensor 104 may be stored at 15 to 25° C. for more than 1 year without loss of functionality. Alternatively, the air-dried, fully functionalized cantilever test sensor 104 may be stored at −20° C. for in excess of one year without loss of functionality. If areas of binding area 330 are free of binding agent 335, dry-stored sensors may require the addition of HEPES and BSA prior to testing.

At step 200, the unmodified cantilever test sensor 102 surface may be composed of Si, or silicon nitride. At step 202, the Si in binding area 330 reacts producing an alcohol functional group on the binding area surface 330. This alcohol surface is replaced with a primary amine surface. The amine surface created at step 204 will form weak, unstable amine bonds that will hydrolyze in blood if reacted with antibody, IgG, RNA, or DNA. At step 206, the primary amine surface is lengthened so that it includes an aldehyde moiety. The aldehyde moiety may be reacted with the bis-hydride at step 210, or the surface may be modified creating a carboxylic acid (—COOH) functional group that is reacted with bis-hydride at step 210.

FIG. 8 depicts the unmodified cantilever reference sensor 102 (shown in FIG. 3) silicon surface at step 200 through step 207. The unmodified silicon surface of cantilever reference surface 102 is non-reactive with organic compounds. The surface of a silicon cantilever surface must be modified to be utilized as a testing device. The silicon surface is converted to a silanol surface upon the addition of a strong oxidizing agent at step 202. The silanol surface from step 202 is converted to a primary amine surface at step 204. Although binding agents 335 (shown in FIGS. 5, 13 and 16) could be bound on the primary amine surface created at step 204, the nitrogen of a primary amine bonds weakly with the carbon of the carboxylic acid. Weak bonds may disassociate readily allowing non-HIV components to bind to the cantilever test sensor 104 (shown in FIG. 22) binding surface.

The rate of reaction between the amine functional group on the surface of the sensor at step 204 with the carboxylic acid of a binding agent 335 at neutral pH levels (which are required to preserve the functionality of the binding agent) is low limiting the amount of binding agent 335 that will actually bind to the amine surface. Carboxylic acids located on binding agents 335 are deprotonated in their native conformations at neutral pH, making them less reactive and less likely to form bonds with the primary amine moiety ($NH_2$) shown at step 204. Carboxylic acid functional groups on binding agents 335 will be protonated and highly reactive at pH of 3-5, but the conformation of the binding agent 335 will be altered at acidic pH levels of 3-5. The altered conformation of binding agents 335 at acidic pH levels increases the likelihood of erroneous bond formation between carboxylic acid moieties on the surface of binding agents 335. Additionally, acidic pH levels will degrade binding agents 335 so that they lose functionality, i.e. they undergo conformational changes that cause them to lose the ability to bind with binding components 350, destroying the reliability of the sensor. If the amount of binding agent 335 bound to the cantilever test sensor surface is low, then the primary amine created at step 204 will be free to bind to non-specific components, including those with in the liquid sample being tested. Human blood, saliva, and urine comprise a complex mixture of proteins, chemicals, liquids and other components. Any test must be highly specific to be reliable. Thus, the low bonding efficiency of binding agents to the primary amine at step 204 requires further manipulation of the binding surface.

At step 206, the primary amine surface of step 204 is converted to an aldehyde surface via treatment with a linker compound, which may be a homo-bifunctional agent such as 1% aqueous gluteraldehyde. Although the aldehyde surface is reactive with binding agents, it non-selectively forms amine bonds with binding agents via a primary amine on the surface of the binding agent. The aldehyde function may bind with an amine functional group on the active site of a binding agent destroying the ability of the binding agent to bind with HIV components 350. Thus, the aldehyde surface created at step 206 must be altered to limit or exclude non-specific binding with binding agent 335.

Aldehydes and ketones react poorly with hydrazines to produce hydrazones. The reaction is very unfavorable and not effective in functionalizing the surface of cantilever beam 140. Either a catalyst should be added to make the aldehyde to hydrazide reaction more favorable, or the aldehyde moiety produced in step 206 must be modified into a functional group so that it will be more reactive. Aniline acts as a catalyst for hydrazide-aldehyde reactions. The aromatic amine of aniline rapidly forms a Schiff base with the aldehyde, effectively increasing the activation of the aldehyde. The aniline is easily replaced by the hydrazide. The addition of aniline to the reaction greater increases the yield and efficiency of aldehyde-hydrazide coupling with up to 90% coupling within just 4 hours. The addition of aniline to the reaction mixture allows step 208 to be omitted from the method of FIG. 8. The addition of aniline in the reaction produces the hydrazide surface of step 210. But, aniline is highly poisonous, oily, colorless substance that brings risks to the manufacturing and production of the functionalized cantilever sensor 104.

If aniline is not utilized, the aldehyde moiety may be converted to a carboxylic acid which is more reactive with hydrazines to produce a hydrazide bond. At step 210, the surface of cantilever beam 140 is converted to a carboxylic acid chemical surface at step 208. This is done via the application of ozone to the surface for a suitable time period. The carboxylic acid surface created at step 208 is highly reactive and readily bonds with amine functional groups. The carboxylic acid functional groups may be reacted with bis-hydrazide via the carboiimide reaction to create hydrazide on the cantilever binding area 330 surface.

Carboiimide or methanediimine is a functional group consisting of the formula RN=C=NR. Carbodiimides hydrolyze to form ureas. Compounds containing the carbodiimide functionality are dehydration agents and are often used to activate carboxylic acids and cause direct conjugation of the carboxylate to a primary amine ($NH_2$) without becoming part of the final amide-bond. The carbodiimide does not become a part of the final amide product produced. The formation of an amide using a carbodiimide is straightforward, but with several side reactions complicating the reaction. The carboxylic acid may react with the carbodiimide to produce o-acylisourea, an intermediate, which can be viewed as a carboxylic ester with an activated leaving group. The —COOH terminus forms an o-Acylisourea intermediate that is a non-stable and active ester that reacts with the primary amine of the hydrazide group on the surface of binding area 330. The by-product of the process is isourea, which may be removed through rinsing the silicon wafer. The o-acylisourea will react with amines to give the desired amide and an urea byproduct. The side reaction of the o-acylisourea produce both desired and undesired products. The o-acylisourea can react with an additional carboxylic acid to give an acid anhydride, which can react further to give the desired amide. Solvents such as dichloromethane or chloroform may be used to minimize this side reaction.

EDC (1-ethyl-3-(3-dimethylaminopropyl)carbodiimide hydrochloride) and DCC (N', N'-dicyclohexyl carbodiimide) are two common carbodiimides. Either may be used in functionalizing the cantilever surface. DCC is not water-soluble allowing the method herein to be performed in a commercial manufacturing environment. All steps of this method except for the modification of binding agent 335 and attachment of binding agent 335 may be performed in a commercial manufacturing environment reducing costs. Both modification and attachment of binding agent 335 must be performed in a structural biology lab or protein chemistry lab.

At step 210, the carboxylic acid moiety produced at step 208 is reacted with bifunctional hydrazides include carbohydrazide compound or adipic dihydrazide. A bis-hydrazide compound is reacted with carboxylate particle population in large excess to prevent particle polymerization during the reaction. The reaction at step 210 produces the a hydrazide (—$NHNH_2$ functional group) surface on beam 140. The hydrazide —$NHNH_2$ functional group binds strongly and efficiently with both aldehyde and ketone functional groups that are on or may be produced on binding agents 335. Binding agents 335, such as IgG, typically lack aldehyde and ketone groups in or near their active site. For example, the hydrazide surface can be utilized to selectively bind with the —COOH terminus of IgG. The IgG terminus is positioned opposite the active site ensuring that the binding agent will maintain functionality upon binding to the cantilever sensor 102 beam 140 surface. This reduces non-selective binding.

Figure 9:
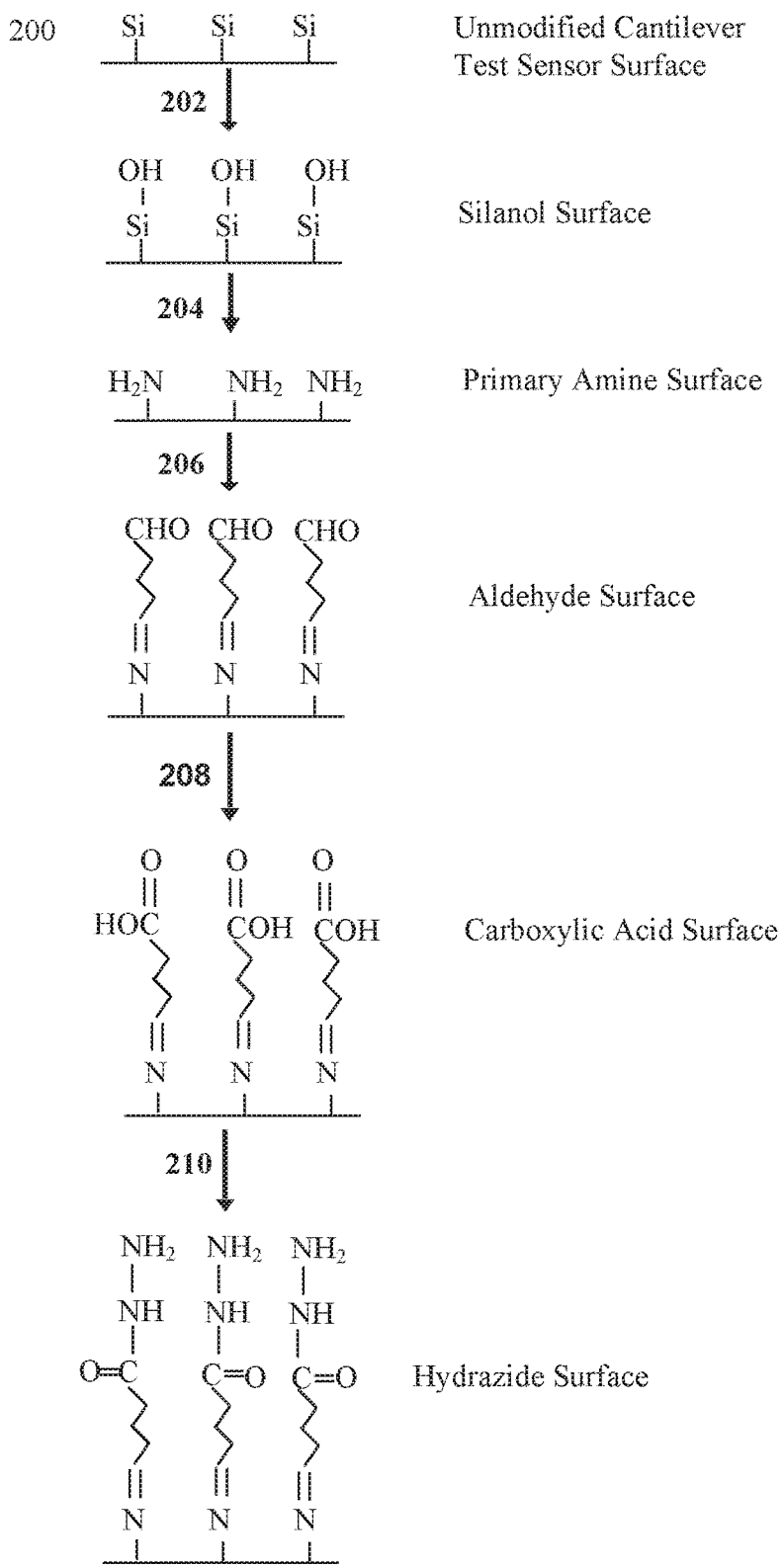
FIG. 9 illustrates the chemical modification of the microcantilever sensor from steps 202 through 210 as depicted in FIG. 8.

FIG. 9 depicts the surface chemistry of steps 200 through 210 of FIG. 8. The surface chemistry is limited to reactions that proceed well at neutral pH because biomolecule binding agents, including IgG, RNA, and DNA, will denature and/or lose conformational or tertiary/quartenary structure at acidic and basic pH levels. Binding agents require a particular conformation to bind with binding components 350 (shown in FIGS. 24 and 26). Any loss of conformation reduces or eliminates binding efficiency with viral components 350 or cancer components 350. Additionally, reactions on the surface of the cantilever test sensor experience different rates of reaction based on pH. If the cantilever test sensor does not have a high rate of reaction, then cantilever test sensor will have surface available for non-specific binding with non-HIV components 350. Non-specific binding destroys the reliability, efficiency, and effectiveness of the device. This device maximizes the efficiency of binding while maintaining the native conformation of binding agents 350.

Figure 10:
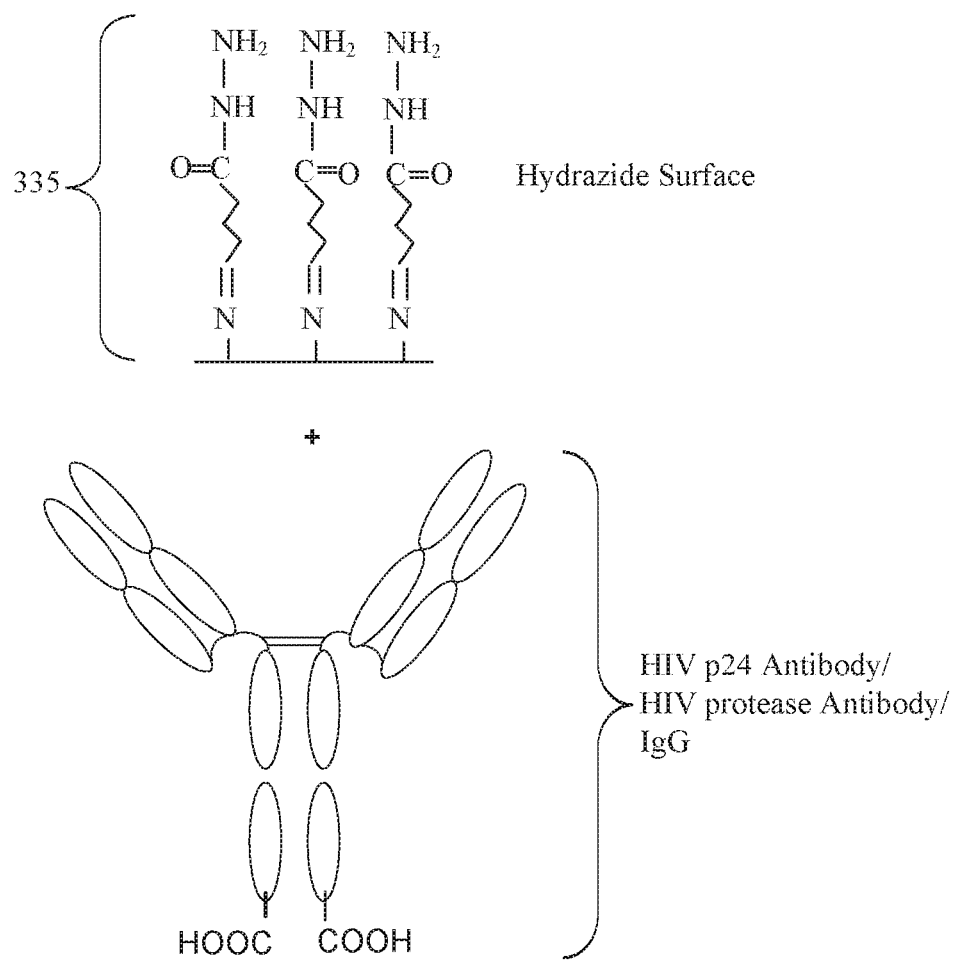
FIG. 10 illustrates the chemical reaction at step 212 of FIG. 8.
Figure 11:
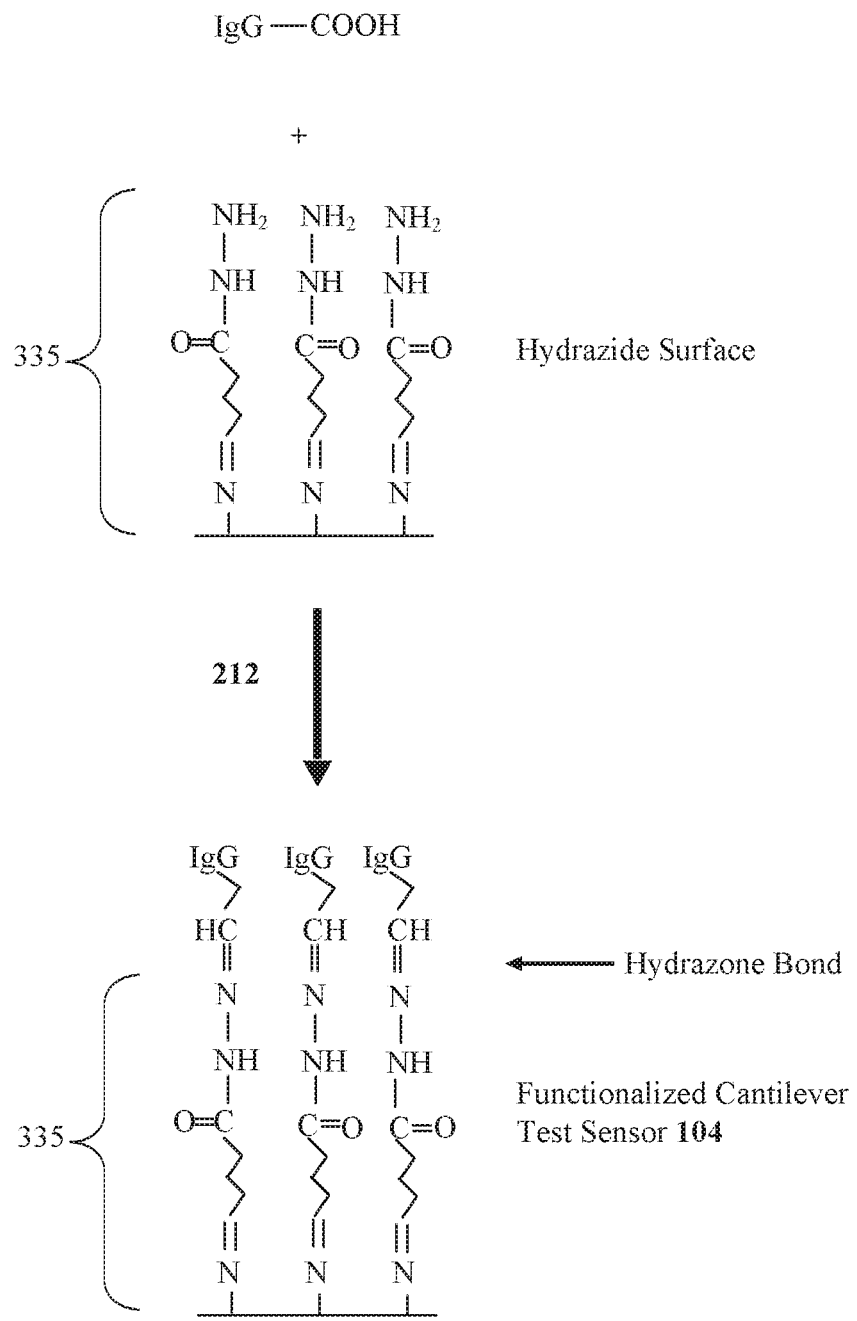
FIG. 11 illustrates step 212 of FIG. 8.

FIGS. 10 and 11 illustrates step 212 of the method herein. In FIG. 10 the chemical combination of IgG, or antibody, binding agent 335 and the hydrazide surface produced at step 210 is shown prior to step 212. FIG. 11 depicts the product of step 212, which is the functionalized cantilever test sensor 104. Binding agent 335 IgG, or antibody, is linked onto the surface of beam 140 with the primary amine ($NH_2$) of the hydrazide surface via reductive amination. The carbonyl groups react with the $NH_2$ to form Schiff bases which can be reduced to form a covalent bond via reductive amination. IgG depicted in FIG. 10 includes two carbonyl (COOH) groups on the terminus of IgG. If IgG does not include glycoproteins or other post-translational modification, then step 222 does not need to be performed, and the IgG can be bound to the hydrazide surface of beam 140 without modification.

FIG. 11 illustrates the hydrazone chemical bond created at step 212 (steps shown in FIG. 8). The hydrazone bond is stable and unlikely to disassociate or to de-protonate at neutral pH. The functionalized cantilever sensor 104 surface is shown in FIG. 11. Note that FIG. 11 depicts the attachment of three IgG binding agents 335 via three hydrazone bonds (C=NNH) on the surface of functionalized test sensor 104. Steps 202 through step 214 create a linker linking binding agent 335 to the cantilever beam 140 surface via the —COOH terminus.

The functionalized cantilever test sensor 104 may be required to be maintained in PBS at step 216. IgG modified at step 222 must retain its native conformation to bind effectively and efficiently with binding components 350. IgG modified at step 222 must be maintained in neutral buffer solution, such as PBS at step 216, to protect the native conformation of IgG. The functionalized cantilever test sensor 104 will be subject to denaturation of binding agent 335 if the buffer solution is not maintained at a certain pH and certain temperature. Any changes in pH or temperature, etc. may destroy the native conformation of IgG, thus destroying the reliability of the testing method and system herein. Whether the functionalized cantilever test sensor 104 must be maintained in buffer solution will be dependent on the IgG utilized as binding agent 335. Some binding agents 335 may be able to maintain their native conformation despite being dried and stored.

An alternate method of preparing a microcantilever sensor includes modification of the aldehyde produced at step 206 into an alkoxyamine (—CH—O—$NH_2$) by subjecting the cantilever to hydroxylamine ($NH_2OH$). This option eliminates steps 208 and 210. The Alkoxyamine created is in the form of geometric isomers with a mixture of both —CH—O—$NH_2$ and —CNOH. Only the —CH—O—$NH_2$ isomer is reactive with the modified binding agent. The addition of certain catalysts can be added to control the reaction to produce the —CH—O—$NH_2$ isomer. The alkoxyamine created is then reacted with the modified binding agent at step 212 to create a fully functionalized sensor 104 that may be maintained in HEPES buffer until use.

Optionally, nucleic acids can be reacted after step 206 with hydroxylamine to create alkoxyamine —CH—O—NH$_2$ functional group(s) on the surface of the microcantilever. This optional method of preparing a nucleic acid microcantilever allows the elimination of steps 208 and 210. The alkoxyamine group formed on the cantilever is then reacted with modified binding agent at step 212 to create the fully functionalized cantilever sensor 104. Functionalized cantilever sensor 104 may then be dried and stored, or maintained in HEPES buffer until use. Storage in buffer eliminates the need of a user to add buffer solution to test well 4 prior to use reducing user error and buffer storage. Nucleic acids can be maintained in buffer for a lengthy period while maintaining their structural integrity.

Figure 12:
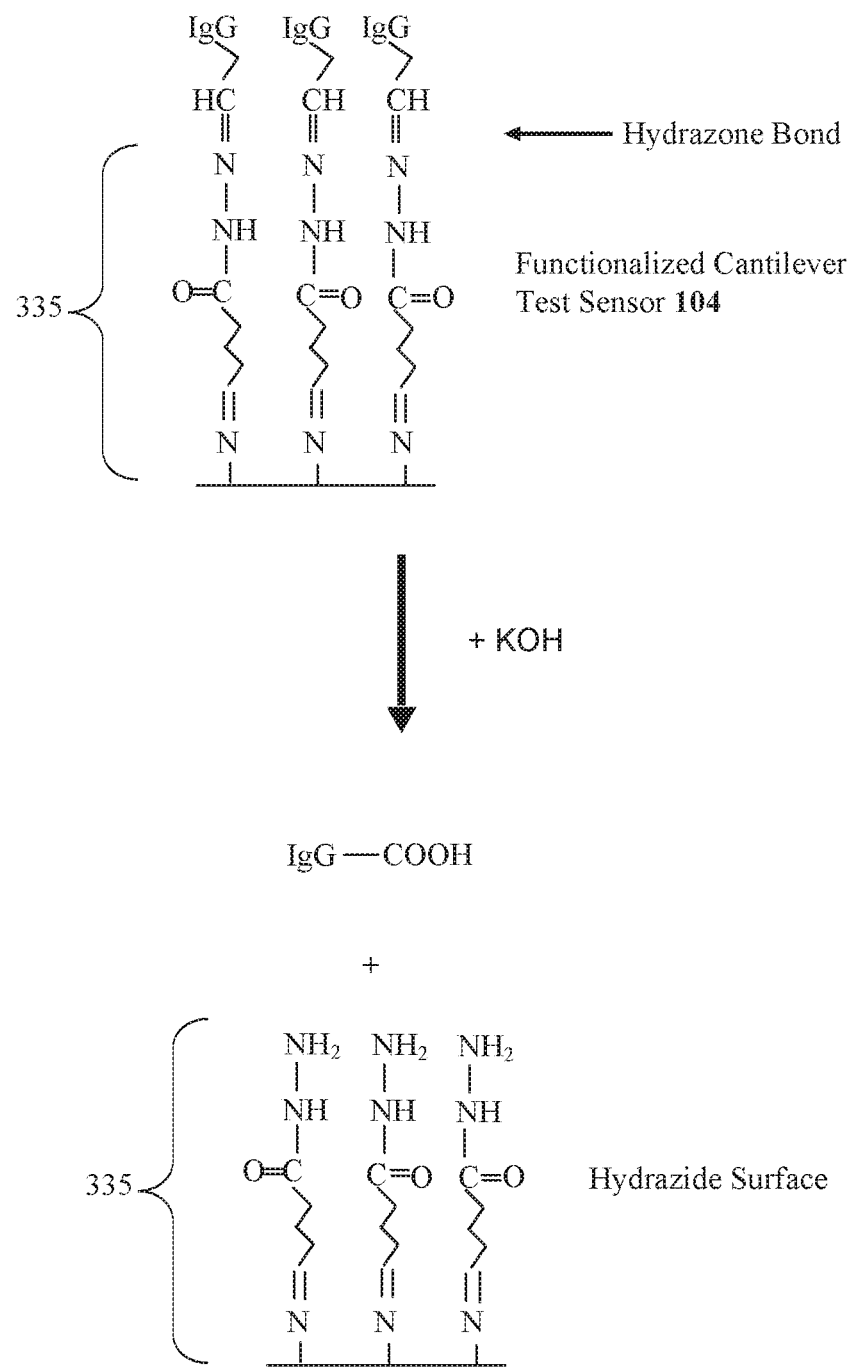
FIG. 12 depicts the regeneration of the functionalized test sensor with KOH.

Hydrazone bonds are stable at blood pH, but highly unstable at high pH. FIG. 12 depicts the regeneration of the PEMS microcantilever test sensor 104. KOH is added to test well 4, which contains the functionalized PEMS cantilever sensor and bound IgG. The hydrazone bond is cleaved so that bound IgG (and any binding component 350 attached to binding agent 335) is released from the PEMS microcantilever surface regenerating the hydrazide surface. The surface of cantilever beam 140 is regenerated to the aldehyde surface of step 206. This allows the cantilever surface to be regenerated via steps 208 through 212.

Most viruses that infect humans are single-stranded RNA (ssRNA) viruses. Some of these ssRNA viruses are naked, while others are encapsulated or enveloped. Blood taken from patients infected with both naked and enveloped ssRNA viruses contain viral RNA. This viral RNA can be detected by the method herein. The detection of the presence of viral RNA indicates viral infection. This method may be utilized to detect the presence of viral RNA which occurs before the production of antibodies.

Native viral ssRNA is not reactive with the surface of cantilever beam 140. RNA will not bind to hydrazide (NHNH$_2$) absent chemical modification. Therefore, native viral ssRNA must be modified so that it will be reactive with the surface of cantilever beam 140, and will therefore bind onto the cantilever beam 140.

FIG. 13 depicts the modification of viral ssRNA. The ribose sugar of RNA is a reducing sugar. Dissolved sodium periodate (NaO$_4$) is a well known mild agent for effectively oxidizing vicinal diols in sugars, including ribose sugar, to yield reactive aldehyde groups at step 224. The carbon-carbon bond of the ribose sugar is cleaved between the adjacent hydroxyl groups. A concentration of 1 mM periodate may be used to ensure that only the end of the single strand of RNA nucleotide is modified with two aldehyde functional groups preserving the binding area of the ssRNA. The addition of periodic acid for a short duration at step 232 oxidizes the 3' terminus of complementary RNA to create vicinal diols that reacts with hydrazide surface of beam 140 produced at step 210 to create the hydrazone bond of step 212.

Figure 14:
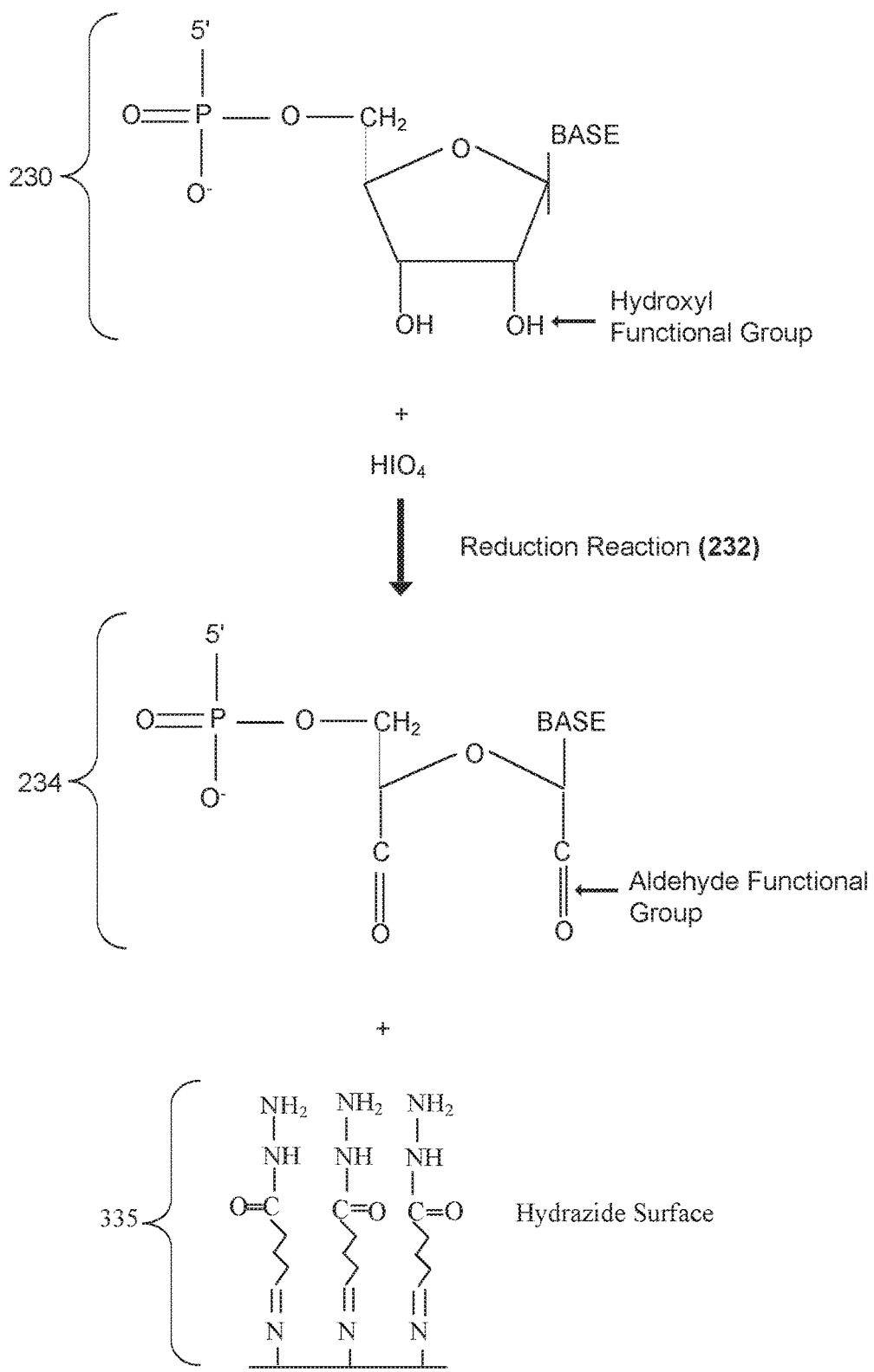
FIG. 14 depicts the chemical structure of steps 232 and 212 as depicted in FIG. 8.
Figure 15:
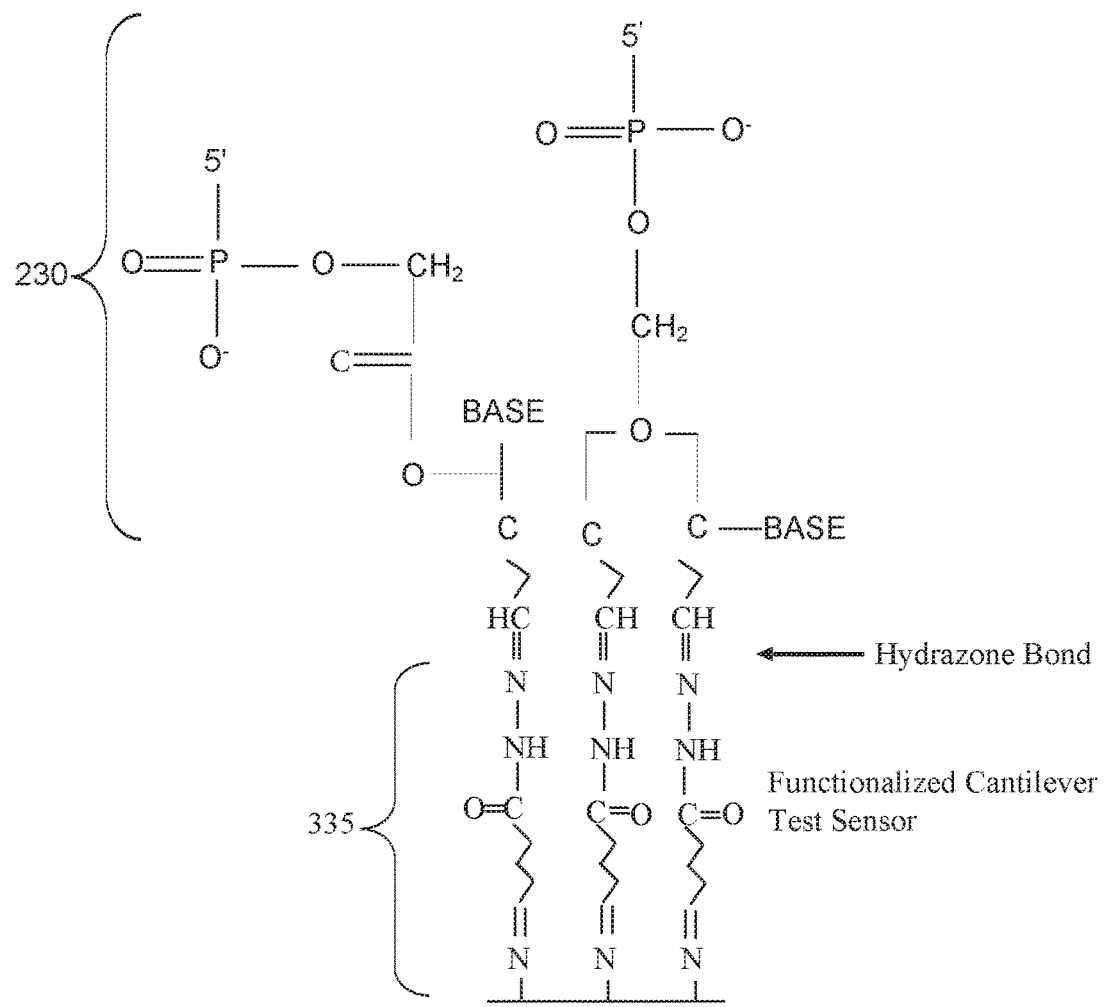
FIG. 15 illustrates the functionalized PEMS microcantilever test sensor surface 104 with RNA binding agent 230 bound via a hydrazone bound.

FIG. 14 illustrates the chemical reduction of RNA complementary to HIV RNA with periodic acid. Note that the two hydroxyl functional groups located on the 3' end of the RNA strand are reduced forming two aldehyde functional groups on the 3' end. Each of the two aldehyde groups are reactive with the hydrazide surface of cantilever beam 140. The functional aldehyde group is shown reacting with the chemical hydrazide surface of cantilever sensor. FIG. 16 depicts the functionalized cantilever test sensor 104. FIG. 15 depicts two ssRNA strands bound to the cantilever beam 140 surface via three hydrazone bonds. Note that one ssRNA strand is bound via two hydrazone bonds, while a second ssRNA strand is bound via a single hydrazone bond. Cantilever test sensor 104 is fully functionalized with RNA binding agent (which is complementary to HIV ssRNA) is shown in FIG. 15. Note the length of the chemical linkage to the silicon surface of binding area 330. A lengthy linkage promotes binding of binding components 350, thus enhancing the efficacy of the device. Short linkages inhibit cantilever test sensor 104 efficacy. The hydrazone bond formed with RNA binding agents 335 is strong and unlikely to disassociate at neutral blood pH.

ssRNA is stable for long periods. ssRNA is stable for approximately 2 years if maintained at −20° C., whether dry or in solution (water or TE buffer). ssRNA may be maintained for approximately 1 year at 4° C., whether dry or in solution (water or TE buffer). And, ssRNA is stable for approximately 3-6 months, whether dry or in TE buffer, at room temperature, and can be maintained at hot room temperatures (non-temperature-controlled shipping or storage in warehouse) for approximately 1-2 months, whether dry or in TE buffer. The stability of the functionalized cantilever test sensor 104 with bound ssRNA binding agent 335 means that this device can be utilized in sub-tropical and tropical locales without access to refrigeration and temperature-controlled shipping/storage facilities. This allows test sensor head 7 to be utilized in very remote, undeveloped areas that current lack testing resources. RNA functionalized sensors do not require step 216, immersion and storage in BSA.

HIV is a single stranded RNA virus of ~9,000 bases. There are three classes of RNA produced during the expression of the HIV-1 prodical genome. The shortest class (~2 kb) are doubly spliced transcripts that are produced early in gene expression coding for the regulatory genes tat, rev and nef; a singly spliced transcript (~4 kb) encoding the genes for structural proteins env, if, var. and you; and a full-length unspliced RNA (~9 kb) coding for gag/pol. Each of these three classes contain the first 290 residues of RNA. HIV-1 leader RNA is the extreme 5'-end 59-residue stem-loop, the trans-activation responsive element TAR, which is highly conserved. Below is the tar region of the RNA genome:

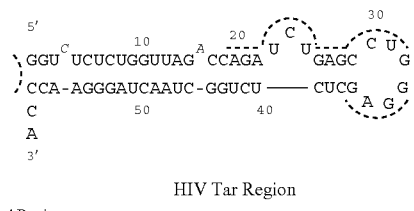

HIV Tar Region

--- Targeted Region

RNA oligos of ~40 to 60 bases that are complimentary to the TAR region may be readily purchased from a number of oligo manufacturers, or prepared from the following primers: 5'-GGUUACCAGCCCACUGC-3'; 5'-UCUAAUAC-GACUCAC UAUAGGUUACCAGCCUUCACUGC-3'; and 5'-GUGUGACCGACCGUGG UGC-3'. Each of these primers may be used to produce the following sequence that allows binding to the stem loop structure of the TAR region: 5'-GUCCCAGA-3', which is the consensus motif constituting the apical loop. This sequence is complimentary to the TAR region and will bind to HIV RNA TAR at blood physiological magnesium levels and physiological temperatures. The temperature of the blood sample may be increased slight to 40-60° C. to enhance annealing of the 5'-GUCCCAGA-3' consensus binding agent 335 with HIV components 350.

HIV RNA includes a long terminal repeat (LTR) area of 634 bp in length. The LTR is segmented into a U3, R, and U5 regions. The following sequence is complimentary to the U5 region of the LTR of HIV and may be utilized as binding agent 335: 5'-CCAGAGUCACACAACAGACGGGCACA-3'. DNA or RNA complimentary to this sequence, or anti-U5 sequence, may be utilized as binding agent 335. The 3' adenine is reduced at step 232 by a mild reducing agent producing two vicinal aldehydes on the 3' end of the anti-sense sequence. Next, at step 212, the aldehyde moieties are coupled to beam 140 surface via the formation of a hydrazone bond. This anti-U5 sequence will bind with the U5 region of HIV binding components 350 at blood pH, salt and ion levels, at biological temperature.

HCV is a single stranded RNA virus comprising a RNA strand of ~9.6 kb that encode approximately 3,000 amino acids. HCV RNA encodes highly conserved essential non-translated regions (NTFS) at the 5' and 3' ends that encode essential regulatory signals for initiating anti-genomic (3'NTR) and genomic (5NTR) RNA synthesis. HCV RNA may be present and detectable prior to the production of antibodies.

HCV RNA may occur at significant levels in the blood of a infected person. Currently, HCV infection is characterized as either a "high" viral load, which is usually a viral RNA load greater than 800,000 IU/L, or a "low" viral load, which is usually <800,000 IU/L. Viral load is quantified because patients with a low viral load respond better to treatment. This test can be utilized to both determine infection qualitatively, and the viral load can be determined quantitatively. During active infection, viral loads are typically greater than 100,000,000 IU/L, or 5,000 virons per drop of blood. The large number of virons per drop of blood makes HCV RNA easy to detect upon dilution in test well 4 containing buffer solution.

Exemplary 5' non-coding regions of HCV that may be detected in a blood sample may include 5'-CUGUGAG-GAACUACUGUC-3' (detected with its antisense: 5'-CAC-UACUCGGCUAGCAGU-3'), 5'-CACGCAGAAAGCGU-CUAG-3' (detected with its antisense: 5'-UUUAUCCAAGAAAGGACCC-3'); using probe: 5'-AGUAUGAGUGUCGUGCAGCCUCCAGGA-3'. Multiple anti-sense probes may be employed as binding agent 335. The 3' adenine ribose is reduced at step 232 to produce two vicinal aldehydes. The vicinal aldehydes are coupled to the cantilever beam 140 surface at step 212 via the formation of a hydrazone bond.

A number of viruses are known to cause viral hemorrhagic fever (VHF). These viruses include: Ebola virus, Marburg virus, Lassa virus, Junin virus, Machupo virus, Sabia virus, Guanarito virus, Crimean-Congo hemorrhagic fever virus, Rift Valley fever virus, Hanta viruses, yellow fever virus, and dengue virus. These viruses are single stranded RNA viruses. VHF are endemic to subtropical and tropical regions. VHF are difficult to diagnose until absent bleeding or organ manifestation. PCR has been successfully applied to the detection of VHF. VHF RNA can be detected in the blood of infected individuals using RT PCR. However, PCT is not readily available in most subtropical and tropical locations where you find VHF infection. A method of identifying VHF infection that can be utilized in the field will assist in diagnosis and early treatment, and reduction of pandemic infection.

The method herein can be utilized to produce a PEMS microcantilever sensor that is capable of detecting VHF presence in blood, thus allowing diagnosis of infection. Ebola virus is a negative sense virus of ~18.96 kb in length. The following exemplary antisense sequences may be reduced at the 3' end to allow attachment to the surface of beam 140 via a hydrazone bond: 5'-AUCGGAAUUUUC-UUUCUCAUU-3' and 5'-AUGUGGUG GGUUAUAAUAAUCACUGACAUG-3'. These antisense sequences or utilized as binding agents 335 because they selectively bind with the Ebola RNA strand isolated from the blood and semen of infected individuals. Other sequences have been identified that may also serve as binding agents 335 upon reduction of the 3' end with a mild reducing agent. RNA is highly stable and unlikely to decompose upon drying. Once bound to the surface of beam 140, the cantilever sensor may be dried and stored. The cantilever test sensor 104 with for detection of RNA can be transported long distances deep without refrigeration or expensive storage protocals within subtropical and tropical locales to be used at the point of contact with the patient.

Additional antisense sequences have been identified for other VHF viruses. These sequences can be reduced by a mild reducing agent, and adhered to the PEMS microcantilever surface via a hydrazone bond.

FIG. 16 is flow chart depicting the modification of DNA, that is complimentary to binding component 350, which may be complimentary to viral RNA, viral DNA, ctDNA, or other RNA or DNA. DNA binds to complimentary RNA and to complimentary DNA. Native DNA will not bind to cantilever beam 140 without modification. This method utilizes single stranded DNA. Single-stranded DNA is produced by raising the temperature of the solution containing the double-stranded DNA up to the temperature of denaturation (which will differ based on the content of the DNA double strand). The temperature of denaturation is the temperature at which the hydrogen bonds between the two strands of DNA break creating two single strands of DNA.

Double-stranded DNA produced via PCR may be maintained at the denaturation temperature during step 232, creating single stranded DNA that may be reduced at the 3' end. Alternatively, double-stranded DNA may be reduced via step 232, then raised to the denaturation temperature while performing step 212. The complimentary strand of DNA is modified so that it will react and bind with the hydrazide cantilever surface produced at step 210, FIG. 8. DNA that is complimentary to viral RNA, viral DNA, ctDNA, etc. is subjected to a mild reducing agent, such as periodic acid ($HIO_4$) at step 232 to oxidize the 3' terminus of the complimentary DNA. The modified single-stranded DNA (ssDNA) should be maintained at the temperature of denaturation during step 212.

ssDNA is stable for long periods. ssDNA is stable for approximately 2 years if maintained at −20° C., whether dry or in solution (water or TE buffer). ssDNA may be maintained for approximately 1 year at 4° C., whether dry or in solution (water or TE buffer). And, ssDNA is stable for approximately 3-6 months, whether dry or in TE buffer, at room temperature, and can be maintained at hot room temperatures (non-temperature-controlled shipping or storage in warehouse) for approximately 1-2 months, whether dry or in TE buffer. The stability of the functionalized cantilever test sensor 104 means that this device can be utilized in sub-tropical and tropical locales without access to refrigeration and temperature-controlled shipping/storage facilities. This allows test sensor head 7 to be utilized in very remote, undeveloped areas that current lack testing resources. DNA functionalized sensors do not require step 216, immersion and storage in BSA.

Figure 17:
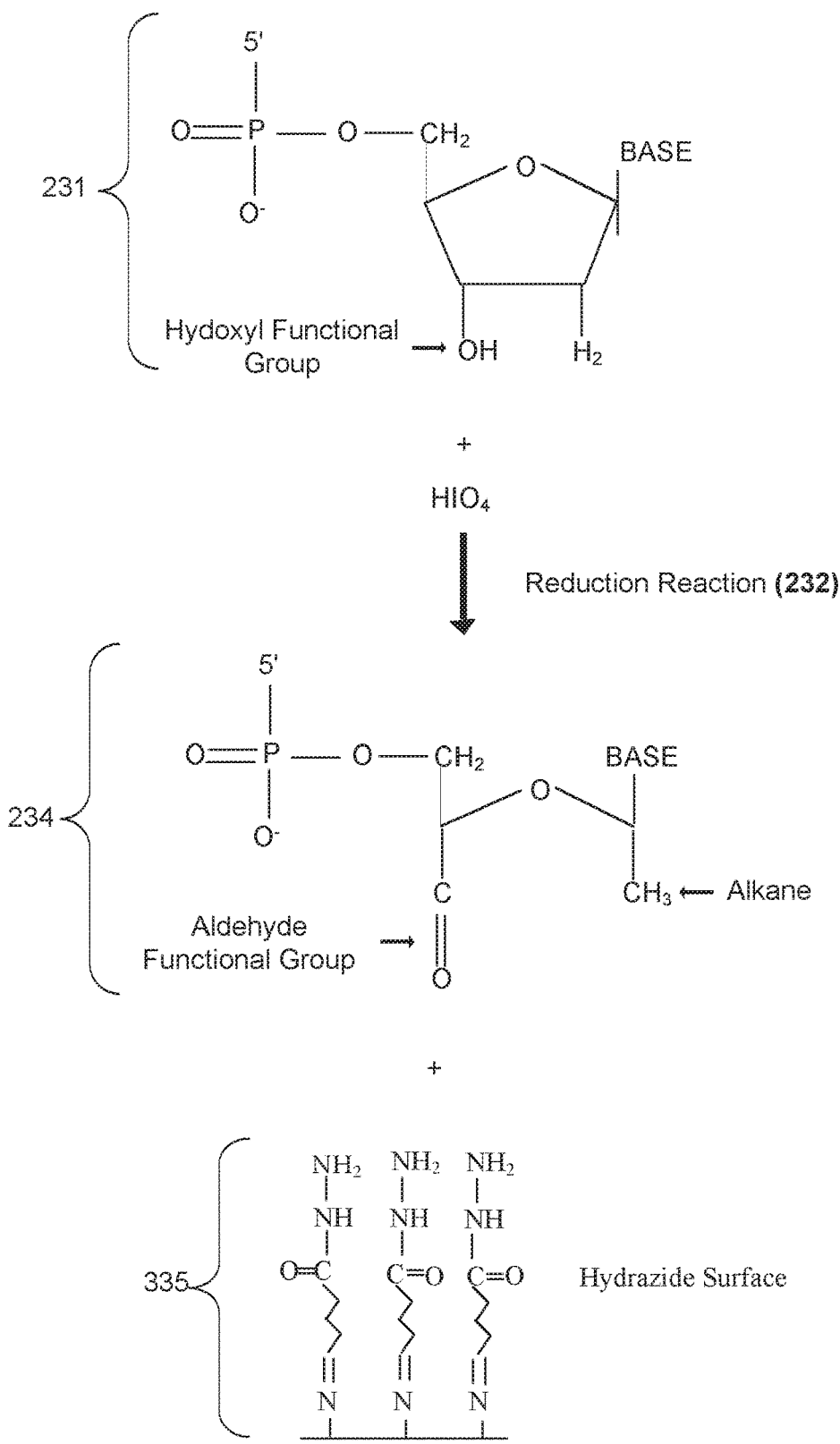
FIG. 17 illustrates the reduction reaction of step 232 depicted in FIG. 17.

FIG. 17 depicts the chemical reduction of the 3' terminus of complimentary DNA to produce the functional aldehyde function at the 3' hydroxyl functional group. Note that the ribose moiety of the 3' terminus of the complimentary DNA strand is reduced breaking the bond between the $C_2$ and $C_3$ carbons creating a single hydroxyl functional group and a alkane. Step 234 yields a single reactive aldehyde functional group on $C_3$ of the 3' terminus of the DNA strand and a non-reactive alkane on $C_2$. At step 212, the aldehyde functional group at $C_3$ is reacted with the hydrazide functional group ($NHNH_2$) produced on the surface of cantilever beam 140 at step 210, which binds the modified DNA strand to the cantilever test sensor 104 via a hydrazone bond. The hydrazone bond created is highly stable and unlikely to disassociate. Thus, ensuring that the cantilever test sensor 104 reliably only binds with binding components 350 instead of other components contained within a sample being tested.

FIG. 17 depicts the chemical modification depicted in FIG. 16. The 3' end of DNA is shown reduced at the 3' hydroxyl functional group via periodic acid. Dissolved sodium periodate ($NaO_4$) is a well known mild agent for effectively oxidizing vicinal diols in ribose sugars, including dioxyribose sugar, to yield reactive aldehyde groups at step 224. The carbon-carbon bond between the hydroxyl group and the proton at the 3' terminus is cleaved. A concentration of 1 mM periodate may be used to ensure that only the 3' end of the single strand of DNA is modified with an aldehyde functional group. An aldehyde functional group is formed at the 3' terminus of DNA. The 3' terminal aldehyde reacts with hydrazide ($NHNH_2$) to create a strong hydrazone bond that links the DNA to the cantilever test sensor 104 surface. FIG. 15 depicts the fully functionalized cantilever test sensor 104 chemical surface with bound DNA.

Figure 18:
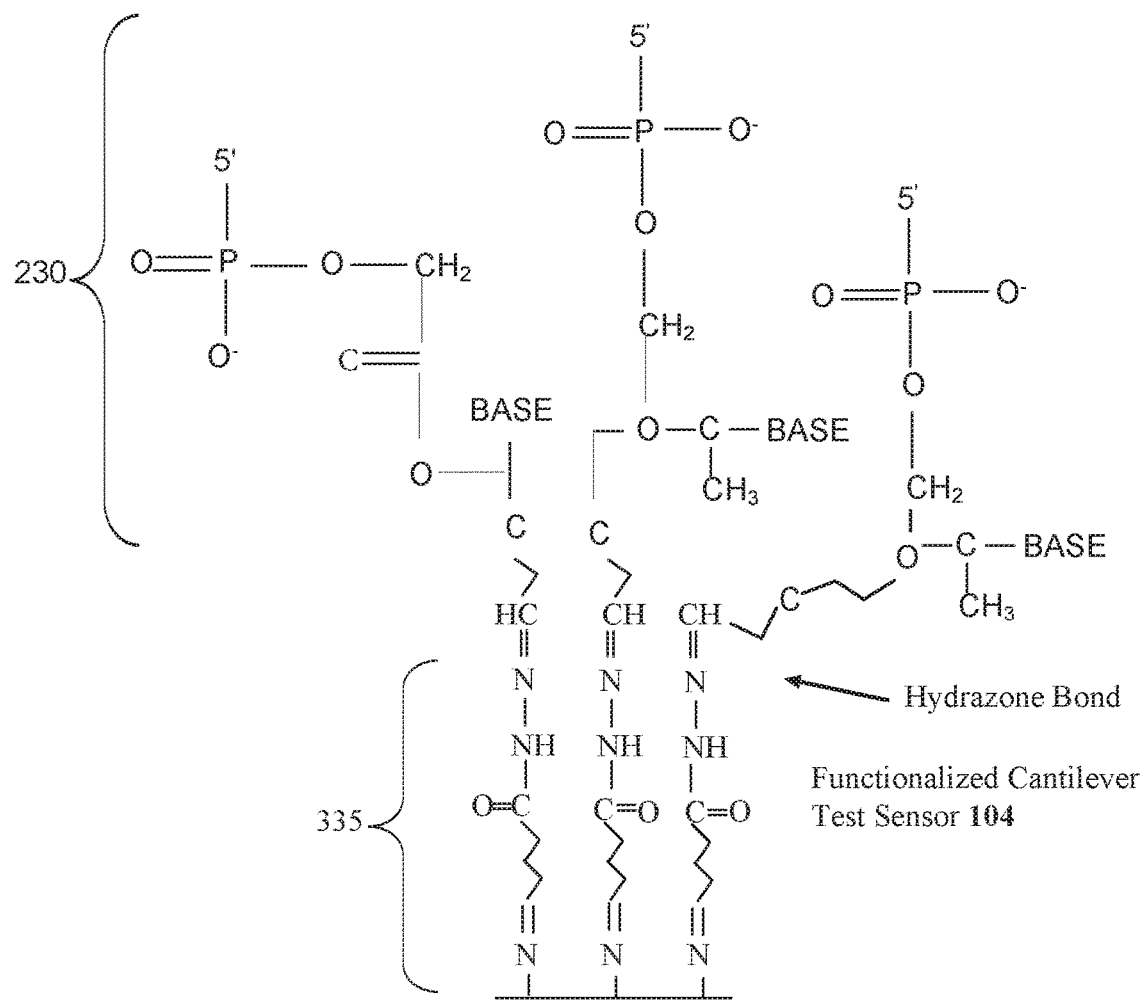
FIG. 18 illustrates the surface of the PEMS microcantilever test sensor 104 with bound DNA binding agent 230.

FIG. 18 depicts three separate ssDNA strands bound to the cantilever test sensor 104 beam 140 surface via strong hydrazone bonds. The 5' end of the ssDNA strands is not chemical reactive with the hydrazide surface. The functionalized cantilever test sensor 104 with bound ssDNA may be dried and stored for up to two years, as set forth above.

Although HIV RNA is single stranded, it will bind with both ssRNA or ssDNA. The antisense RNA sequences previously listed can be modified so that they are ssDNA antisense strands that will bind to HIV ssRNA. For example, the TAR region RNA primer can be modified to a ssDNA primer: 5'-GGTTACCAGCCCACTGC-3; 5'-TCTAATAC-GACTCACTATAGGTTACCAGCCTTCACTGC-3; and 5'-GTGTGACCGTCCGTGGTGC-3'. Each of these three ssDNA sequences can be modified at their 3' ends so that an aldehyde is formed at the $C_3$ location. The aldehyde at the $C_3$ location can then be reacted with the hydrazide surface of cantilever beam 140 to form the functionalized cantilever test sensor 104.

5' non coding regions of HCV can be detected using ssDNA adhered to the cantilever surface via hydrazone bonding. For example, 5'-CACTACTCGGCTAGCAGT-3' and 5'-TTTATCCAAGAAAGGACCC-3' may be utilized as binding agents 335 to detect HCV. Although the following sequence: 5'-CACTACTCGGCTAGCAGT-3', has a mass of just 5.49 kDa, the viral HCV ssRNA that it will bind to has a much greater mass. Thus, the binding of viral HCV ssRNA will be detectable by the PEMS cantilever sensor herein.

VHF can be detected using ssDNA that will bind to the viral VHF ssRNA. For example, if 5"-ATCG-GAATTTTCTTTCTCATT-3' may be used as binding agent 335. The antisense sequence 5"-ATCGGAATTTTCTTTCT-CATT-3' has a mass of 6.35 kDa. The antisense DNA sequence will bond with viral VHF ssRNA, which has a much greater mass, creating both deflection in the sensor and a change in resistance that may be detectable by monitoring the output voltage of a functionalized cantilever sensor 104.

Dengue virus is an arthropod-borne human viral pathogen that has become a major public-health burden in tropical and subtropical areas of the world, mostly in Southeast Asia and Western Pacific Regions. Those infected with dengue may be asymptomatic or may experience life-threatening dengue shock syndrome. Approximately 50-100 million dengue infections are estimated to occur annually, including about 250,000-500,000 cases of dengue shock syndrome. Mortality from infection can be 10-20% of severe cases. Currently, there is not an effective vaccine or antiviral treatment. But, early can reduce the mortality rate from 10-20% to less than 1%. Dengue shock syndrome is characterized by an increase in cell free DNA (cfDNA). The increase in cfDNA may be detected by the cantilever test sensor 104 if the binding agent 335 is complimentary to cfDNA being detected. Test well 4 permits a known quantity of fluid to be added with the blood sample being testing. Having the quantity of blood and the quantity of buffer allows the concentration of cfDNA to be computed.

Many cancers harbor genetic mutations. Certain genetic mutations respond to a particular treatment modality more favorably than other genetic mutations. For example, some ovarian cancer patients harbor a BRCA1/2 mutations that responds favorable to poly (ADP-ribose) polymerase 1 (PARP1) inhibitors while other non-BRCA1/2 patients do not. A method of screening genetic mutations in cancer patients is needed. The method should be rapid, cost-effective and non-invasive. The current method of mutation screening requires biopsy of the cancer and gene sequencing of the biopsied material.

ctDNA derived directly from the tumor circulates in a patient's blood. ctDNA includes all of the subclones in a tumor, including the presence of mutated genes. ctDNA may exist as ssDNA or dsDNA. This method allows the detection of single-stranded ctDNA of a minimal length. Currently, PCR is performed on blood samples of cancer patients to detect the presence of certain genetic mutations, including detection of some ctDNA mutations. Ovarian and breast cancer patients with BRCA1/2 mutations may have one of many BOCA variants. See BIC database, BOCA Share™ database, Elinvar and/or the HGMD. Ovarian and breast cancer patients with certain mutations respond differently to certain cancer treatments. This method can be utilized to determine whether a patient has a particular genetic mutation that would suggest a particular treatment modality.

In order to identify a single mutation/variant, multiple PCR tests would have to be performed in a laboratory. This is time consuming and expensive. PEMS microcantilever detection allows a single test to include multiple test sensors wherein a single test can include a number of different individual test sensors. For example, in the BRCA1 example above, one PEMS sensor may be configured to detect the ctDNA mutation at 181T>G, a second single PEMS sensor may be configured to detect the ctDNA mutation at 1693G>T, a third single PEMS sensor may be configured to detect the ctDNA mutation at 3296delC, a fourth single PEMS sensor may be configured to detect the ctDNA mutation at 3700_3704del; and a fifth single PEMS sensor may be configured to detect the ctDNA mutation at 3756_3759del. In this way a single PEMS test would include 5 individual mutation screenings. The number of screenings is limited by the number of cantilever sensors utilized in a probe configuration. This allows for rapid screening of cancer mutations while reducing the laboratory time expended. Rapid screening translates into more efficient dosing of chemotherapeutic reagents, preventing unwarranted exposure to chemotherapeutic reagents and allowing quicker correct dosing. Additionally, this model allows for multiple highly pathogenic mutations to be placed within a single test so that patients with a greater risk for a poor outcome can be readily identified.

As noted above, BRCA1 ct mutation at 181T>G is a deleterious mutation identified in some cancers. The following exemplary antisense primer sequences by be utilized as binding agent 335: 5'-GGTGAAGGCCTCCTGC [181] CCGCAGGGGCCCAGTT-3' (note that the T>G mutation at 181 is noted in brackets). This primer sequence can be bound to the cantilever surface of beam 140 via formation of a hydrazone bond. The primer is reacted at neutral pH with the hydrazide surface. A second cantilever test sensor testing for the BRCA1 1693G>T mutation the may have the following binding agent 335: 5'-TCCCTGTCTTTCCCGGAC-CAA[1693] AGGATTTCTGTTGAAAA-3' (note the G>T mutation at 1693 is noted in brackets). A third cantilever surface with the 3296delC mutation may be tested for with the following cantilever binding agent 335: 5'-AACTT-GACTTGAAATAT [3296] AAAAACAACTTTCATAA3' (note the deletion at 3296 as noted in brackets). Each of these mutations, and more, may be simultaneously tested by a single test by having multiple functionalized cantilever sensors 104 included in a single test. The width of the cantilever sensors is so small that a single test may include a hundred, or more, single test sensors.

The preparation of binding agent 335, wherein the binding agent 335 is 5'-GGTGAAGGCCTCCTGC [181] CCGCAGGGGCCCAGTT-3', is performed by subjecting the antisense primer to reduction by periodic acid to oxidize the 3' terminus creating an aldehyde moiety on the 3' end and an alkane. The aldehyde created at step 232 is then reactive with the hydrazide surface on beam 140. The entire process prior to the reduction of the DNA strand may be performed in an industrial manufacturing capacity. The reduction of the ssDNA antisense nucleic acid is performed in a biology/structural biology/protein chemistry lab. Phage and other unseen agents routinely infect biology labs, etc. The costs associated with performance of steps in biology/structural biology/protein chemistry labs is high due to sterility requirements and detail to handling of specimens and laboratory chemicals. Thus, performance of the steps prior to reduction of ssDNA in a commercial manufacturing environment dramatically reduces costs and reduces the likelihood of test sensor contamination.

Upon reaction of the reduced ssDNA with the hydrazide surface, the ssDNA is bond tightly to the cantilever surface. The functionalized cantilever test sensor 104 may be dried and stored for up to two years. ssDNA is highly stable upon drying. The functionalized cantilever test sensor 104 may be maintained at room temperatures or be transported in an unrefrigerated distribution system, which further reduce costs.

ctDNA concentration increases correspondingly as disease progresses. During early disease, ctDNA concentration may be so low that mutation screening is not possible. In these situations, the concentration of ctDNA may be increased. One method of increasing the concentration of ctDNA is to subjected the patient specimen to PCR with a multitude of primers, wherein each primer reflects a different mutation. The PCR product with multiple primers could then be subjected to PEMS cantilever sensor testing. In an alternate method, a larger specimen could be obtained from a patient and the sample subjected to centrifugation so that only the layer containing ctDNA is subjected to the DNA probe. Both of these additional steps allow the multiplication of mutated ctDNA to detectable level while allowing a single test to test for multiple mutations, thus reducing multiple PCR tests to a single PCR test with a single PEMS microcantilever test.

Figure 19:
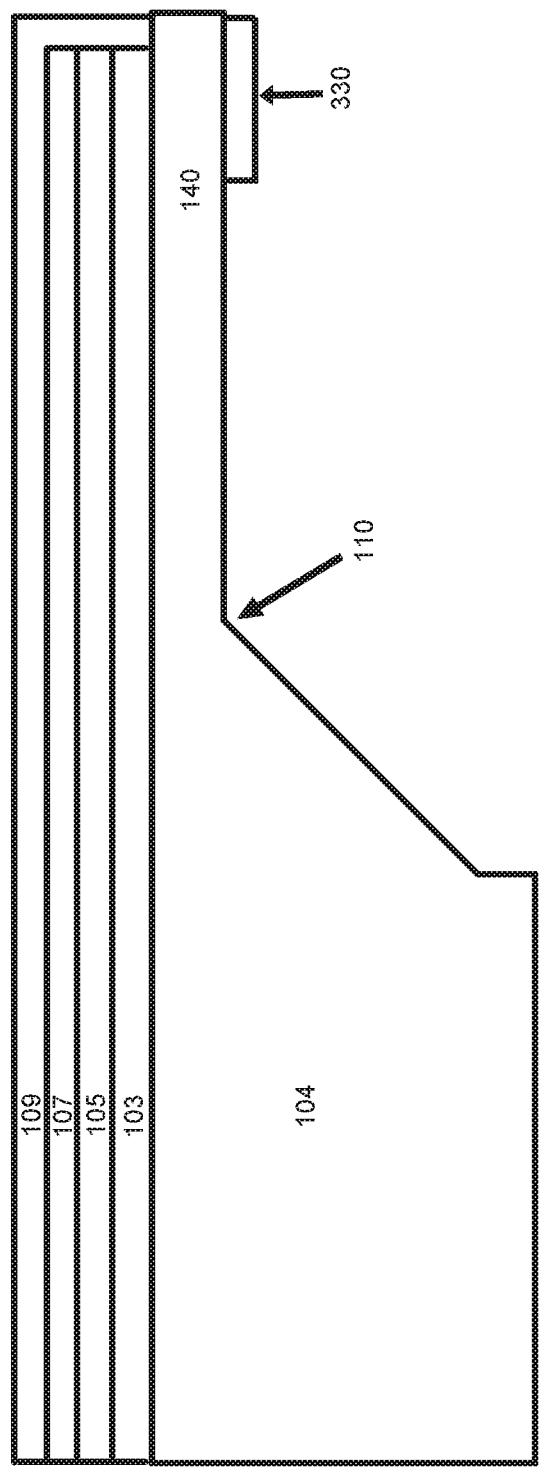
FIG. 19 depicts the PEMS microcantilever reference sensor 102.

FIG. 19 depicts the PEMS microcantilever test sensor at step 208. Binding area 330 may be any length and width within the length and width of the sensor. All areas of the cantilever sensor, except for binding agent 330, are non-reactive with biological and biochemical compounds in aqueous solution, such as blood. Biological agents will only react with areas of the binding area 330 that have been modified to do so. Binding agent 330 may be created by micro printing so that all steps from 202 to 212 are performed in a lone microsite. This limits the use of agents, such as BSA, that prevent unwanted binding. Additionally, ensuring that all steps are performed to completion will reduce the likelihood of non-specific binding sites.

FIG. 20 illustrates the functionalized cantilever test sensor 104 with IgG binding agents 335. BSA has been added to prevent non-specific binding on binding area 330 without bound IgG binding agent 335.

Figure 21:
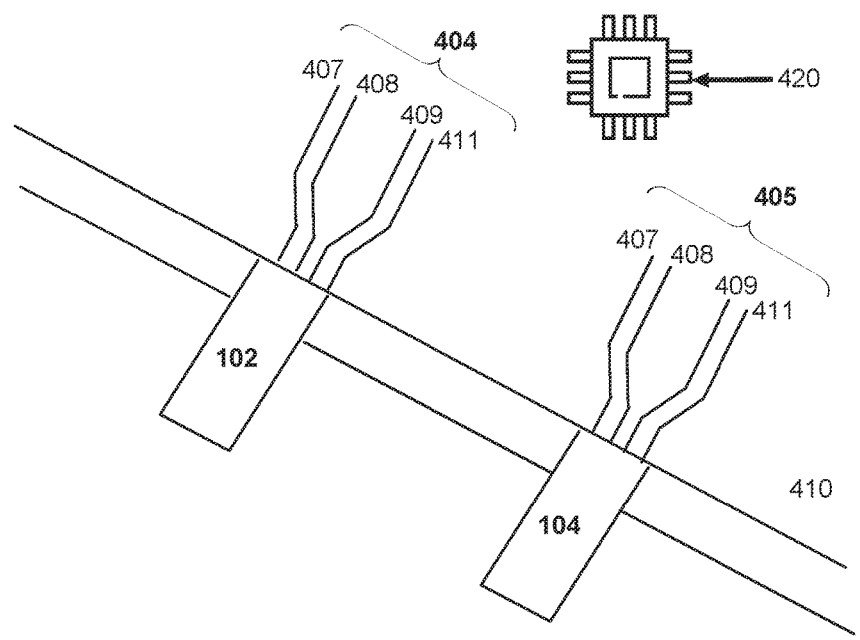
FIG. 21 depicts a cantilever array.

FIG. 21 depicts a PEMS microcantilever sensor array 10. Two microcantilever sensors are shown. In an exemplary embodiment, microcantilever reference sensor 102 is paired with microcantilever test sensor 104. The number of reference sensors 102 and test sensors 104 may be set for the particular use. The number of PEMS cantilever sensors may be increased upon increasing the size of the sensor array 410. For example, the sensor array 410 may include a total of one hundred sensors with ten cantilever reference sensors 102 wherein each cantilever reference test sensor 102 is paired with nine functionalized PEMS microcantilever sensors 104.

Sensor circuit 404 is the control and includes microcantilever reference sensor 102. Sensor circuit 404 includes electric feeds 407 that runs from processor 420 to lower electrode 103 (shown in FIG. 3) of cantilever reference sensor 102 and an electric feed 408 that runs from processor 420 to upper electrode 107. Sensor circuit 404 also includes electric feed 409 that runs from lower electrode 103 (shown in FIG. 3) of cantilever reference sensor 102 to processor 420, and electric feed 411 that runs from upper electrode 107 to processor 420. Cantilever reference sensor 102 will not react/bind with binding components 350 in the aqueous sample allowing the sensor to serve as a reference. Upon the addition of a drop of blood, the voltage outputs at both 409 and 411 of cantilever reference sensor 102 should not change.

Sensor circuit 405 includes microcantilever test sensor 104. Sensor circuit 405 comprises electric feed 407 that runs from processor 420 to lower electrode 103, and 409 that runs from upper electrode 107 to processor 420. Sensor circuit 405 includes electric feed 408 that runs from processor 420 to upper electrode 107 (shown in FIG. 3), and electric feed 411 that runs from upper electrode 107 to processor 420. Upon the addition of a blood specimen into test well 4 (shown in FIG. 1), the output voltage at both electric feeds 409 and 411 should change if the specimen contains binding components 350 (shown in FIGS. 22, 24 and 26).

Each microcantilever sensor (including each cantilever reference sensor 102 and each cantilever test sensor 104) must have an incoming and outgoing electric feed to processor 420. The sensor circuits allow the conversion of resonance/mechanical resistance into a digital electrical signal that can be detected and quantified by processor 420. The device that reversibly connects to test well 4 detects an initial voltage output for both electric feeds 408 and 411 before testing and after the addition of a patient specimen to test well 4 (shown in FIG. 2). If a change in voltage output occurs at electric feeds 408 and 411, then the specimen may contain the binding component 350 sought. Alternate embodiments may include just one electric feed 407 or 408.

Figure 22:
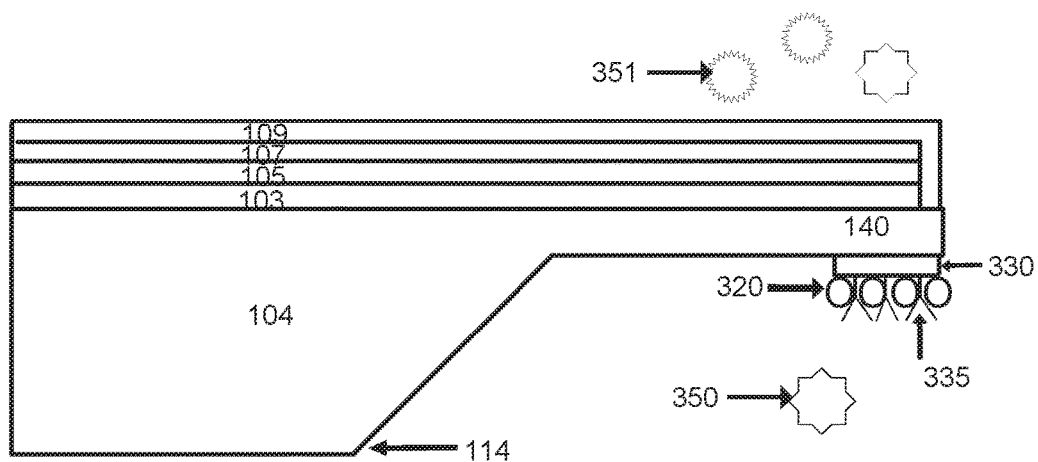
FIG. 22 illustrates a functionalized cantilever sensor with antibody/IgG binding agent 335.

FIG. 22 illustrates a functionalized cantilever test sensor 104 with IgG binding agents 335 bonded onto binding area 330. Binding area 335 covers most of the length of beam 140. Additionally, BSA 320 is bound to all sites on the surface of binding area 330 lacking binding agents 335. Beam 140 is parallel to base 114. An aqueous sample has been added to test well 4 (not shown). The aqueous sample includes both IgG binding components 350 and other blood components 351 that do not bond with IgG binding agent 335.

Figure 23:
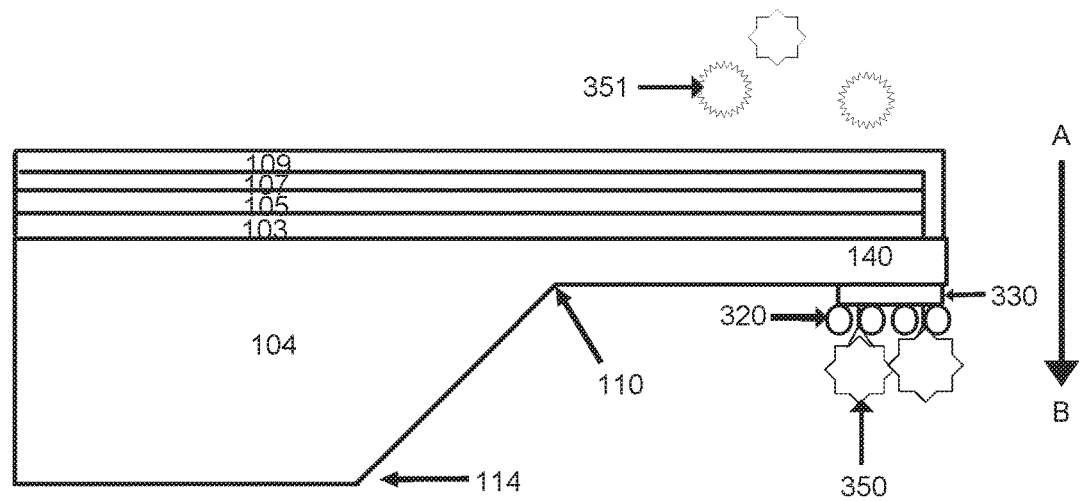
FIG. 23 depicts the PEMS functionalized test sensor of FIG. 23 with antigens bound to IgG binding agents on the surface of the cantilever test sensor.

FIG. 23 illustrates PEMS cantilever test sensor 104 fixed into a PEMS device. Binding area 330 is shown. In this exemplary embodiment, HIV p24 antibody is represented as HIV binding components 350. HIV p24 binding components 350 are bound to HIV p24 binding agents 335 via chemical bonds formed between the HIV p24 in solution and HIV p24 binding agent 335 (which is HIV p24 antibody oxidized at step 222, FIG. 5 that has been attached to the PEMS microcantilever sensor via the method of FIG. 4 or the method of FIG. 8). The HIV p24 binds to the HIV p24 antibody via antigen/antibody binding through chemical interactions, and bonding is essentially non-covalent. Electrostatic interactions, hydrogen bonds, van der Waals forces, and hydrophobic interactions are all known to be involved in antigen/antibody binding/bonding. BSA 320 passivates all areas of binding area 330 lacking bound binding agent 335. Antigen/antibody binding/bonding causes beam 140 to move in the "A" and/or "B" direction relative to base 114 and relative to hinge 110. The mechanical movement or resonance of beam in the "A" and/or "B" direction creates deflection/resonance or a change in resistance that is transmitted as voltage output at electric feeds 408 and 411 to processor 420. Processor 420 converts the change in electrical signal received from electric feeds 408 and 411 into a readout that can be interpreted by a user.

Figure 24:
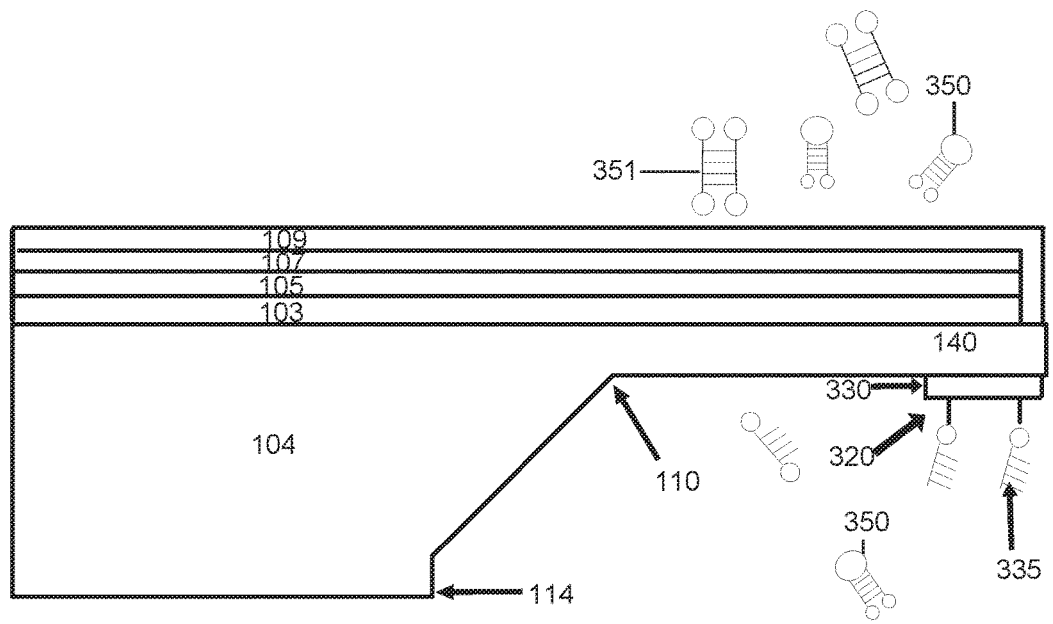
FIG. 24 illustrates the PEMS microcantilever test sensor of FIG. 16 exposed to an aqueous sample containing single-stranded RNA components 350.
Figure 25:
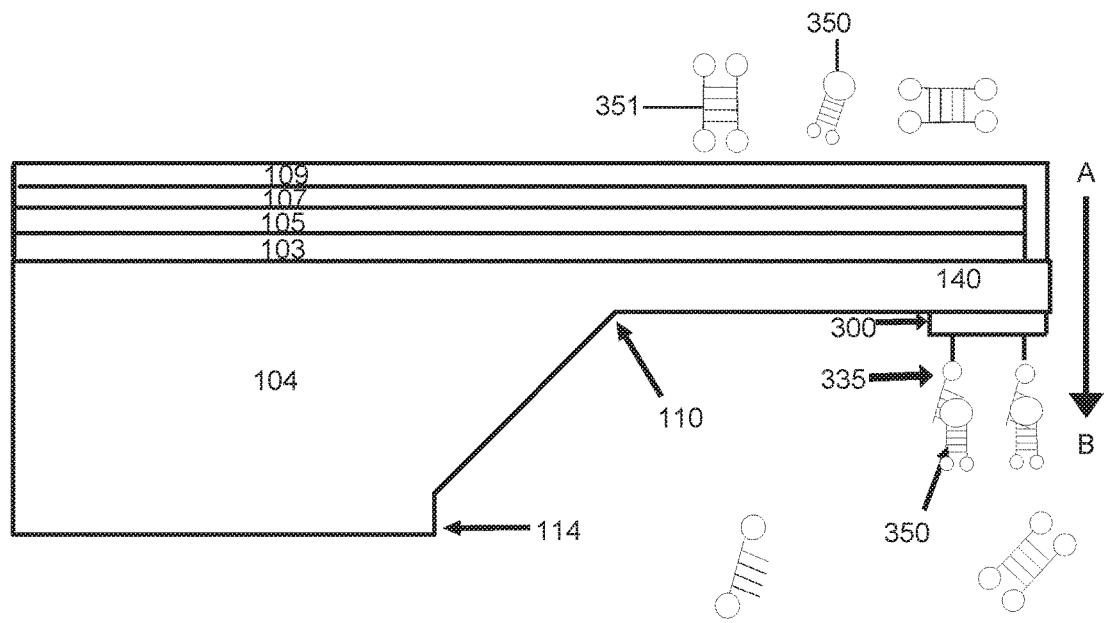
FIG. 25 illustrates the PEMS microcantilever of FIG. 25 upon binding with the stem loop structure of single-stranded RNA nucleic acid components 350 in solution.

In FIG. 24, illustrates an exemplary embodiment wherein functionalized cantilever sensor 104 is subjected to an aqueous solution containing both HIV ssRNA 350 and non-HIV ssRNA 351. Binding agent 335, which comprises ssRNA complimentary HIV ssRNA, is bound to binding area 330. Beam 140 is parallel to base 114. FIG. 25 illustrates the functionalized cantilever test sensor 104 upon binding of HIV ssRNA 350. HIV ssRNA 350, in this example, binds to the HIV ssRNA 350 of the complimentary stem loop structures via base pair bonding, wherein a base in the HIV ssRNA 350 binds to its complimentary base on ssHIV RNA binding agent 335 via hydrogen bonding. No non-HIV ssRNA 351 binds to the binding agents 335. The weight of HIV ssRNA 350 binding to binding agent 335 along beam 140 causes beam 140 to move in the "A" and/or "B" direction. Beam 140 moves about hinge 110 relative to base 114. This movement of beam 140 creates deflection or a change in resistance that is conducted electrically via voltage output at electric feeds 409 and/or 411 to processor 420.

Both the presence and concentration of the HIV-1, HIV-2, Ebola, and/or HCV viral load can be computed using this device. If a virus being tested for is present in the patient sample, then viral components will bind to the binding agents 335 on the surface of beam 140, causing deflection and a change in the resistance over time. This change in mechanical resistance/resonance over time is detectable by processor 420. Processor 420 may quantify the viral load present in a sample because the size of test well 4 is known, the amount of any buffer is known, and the amount of patient sample is also known. Any aqueous patient sample may be used, including, but not limited to blood, urine, or buccal fluids.

Viral load may be determined using this assay. Test well 4 includes a known volume of a patient's blood sample (a single drop of blood) and a known volume of HEPES buffer. Each micro cantilever within the cantilever array has a known binding area 330. The binding area is determined when a user selects whether a level surface micro cantilever or a micro-cantilever with micro-cavities is used. Binding agent 335 applied to the cantilever surface will bind with the hydrazide reagent at applied to the cantilever surface, which was applied at step 208, to produce a strong hydrazone bond at step 210. If micro cantilevers with micro-cavities are employed, then precise measurements can be made so that nano-scale numbers of HIV components 350 can be detected. If a level surface cantilever is used, then a number of tests may need to be completed so that a range of bound virons may be determined. The binding affinity of each virus component (such as CD4, p24, Ebola IgG, etc.) with binding agent 335 under certain conditions (such as temperature, length of time assay is conducted, etc.) should be quantified so that a user knows that "Y" percent of virus component will bind with binding agent 335 under the conditions to be employed. Then, once the assay is completed the difference in value for cantilever reference sensor 102 to cantilever test sensor 104 can be calibrated to the concentration of the tested viron component in the patient's sample. X times Y equals viral load. For example, if modified CD4 binding agent has a binding affinity X (equal to 90 percent or 0.90) and a total binding area 330 of 500 nm, then $4.5 \times 10^{-9}$ binding sites are available. If the binding affinity of viron component Y is ninety percent (or 0.90), then $4.1 \times 10^{-9}$ is the maximum number of bound virons ("Z"). Z represents the limits of a particular test assay configuration. Z can be altered by changing the test conditions, or changing the particular binding agent 335 used in the cantilever test sensor 104. Samples of virus positive blood with differing viron counts can be subjected to the assay so that a particular blood CD4 count can be computed to be a certain percentage of Z.

Upon binding of HIV components with binding agents 335 at time t+1, a change in voltage output at electric feeds 8 and 9, for example electronic circuit 404 or 405 shown in FIG. 18. This change in voltage from t to the value at time t+1. The change at time t+1 is equal to the binding of HIV components to binding agent 335 on the surface of binding area 330 of cantilever test sensor 104. The amount of binding of HIV components is equal to the concentration of HIV components in the sample of blood, urine, or buccal fluid being tested (although concentration of HIV-1 and HIV-2 in urine and buccal fluid may not correlate to HIV-1 and HIV-2 concentrations in a patient's blood). The deflection/resonance and change in resistance value is linear to the HIV component concentration in the sample being tested. Thus, the concentration of HIV may be quantified by this device. The greater the viral load, the greater number of binding sites 335 with bound components, and the greater the change in deflection/resonance or resistance at time t+1. This device can detect the binding of a single HIV-1 viron because the device is able to detect small changes in voltage. HIV IgG binding agent 335 may be stable at room temperatures for up to a month and stable at −4° C. for up to 6 months. This allows the device to be transported and used in remote areas lacking access to reliable refrigeration.

Cantilever array 410 may be comprised of a number of cantilever sensor pairs, which means the device may actually comprise multiple tests within a single test. For example, cantilever array 410 may be composed of two or more pairs of cantilever sensors using IgG as binding agent 335. This would allow for multiple test pairs to accurately quantify HIV-1 viral load. Alternatively, pairs of cantilever sensors may include differing binding agents 335 so that more than one HIV-1 component is tested for in a single test. For example, one pair of cantilever sensors may include a cantilever test sensor 104 with IgG binding agent 335 while a second pair of cantilever sensors may include a cantilever test sensor 104 with antibody IgG p24 binding agent 335. This would allow a single test to test for both IgG concentration and IgGp24 concentration in a patient specimen. At a patient's initial infection, the voltage output computed at electric feeds 408 and 411 of the cantilever sensor pair with IgG binding agent 335 at time t+1 will vary very slightly from the electrical value at time t. But, the voltage output at electric feeds 408 and 411 of the cantilever sensor with antibody IgG p24 binding agent 335 will change significantly from time t to time t+1. Following a patient's initial infection with HIV-1, the voltage output value of IgG binding agent 335 will increase from time t to time t+1, while the voltage output value of antibody IgG p24 binding agent 335 will decrease from time t to time t+1. Months after a patient's initial infection, the voltage output value of the cantilever sensor with antibody IgG p24 binding agent 335 may be unchanged at time t+1 from time t. This device allows both the early detection of initial infection of HIV-1 in a patient and the detection of the progression of HIV-1 infection to be monitored in real time.

Tat protein is a protein associated with the progression of HIV-1 infection to neurological disease. A cantilever test sensor 104 with IgG tat binding agent 335 may be included in cantilever sensor(s) to enable the progression of HIV-1 and related diseases to be monitored in real time.

Patients infected with HIV-1 and HIV-2 are currently prescribed a drug cocktail. The drug cocktail can be both expensive, time-consuming, and difficult for patients to adhere to, and may subject patients to drugs that are not working for them individually. Because viral load can be monitored with great precision, the efficacy of drugs may be monitored with a simple finger prick. This allows a patient's medication to be adjusted so that the reduction in viral load can be maximized without the use of drugs that aren't working for a particular patient. For example, of the dosage of a drug that a patient is being prescribed reduced or the drug is eliminated, the viral load may be monitored to determine if the drug was effective at reducing viral load, or tat levels, etc. If the drug dosage is reduced without any detrimental increase in viral load, tat protein, etc, then the dosage may be maintained at a reduced level. If the drug is eliminated from the patient's drug cocktail, and there is no increase in viral load or other HIV component, then the physician may decide not to use that drug for that particular patient.

Drug efficacy can be monitored using this device. This device utilizes software that may be programmed so that a particular patient's test results may be compared over time. For example, the assay value may be compared before and after certain drug treatment modalities to determine if the drug is aiding the patient. For example, a patient prescribed AZT that has an assay value reflecting an increase in viral load, may be moved to a different treatment modality that is more effective at reducing viral load.

Patients with HCV infection may also be monitored in real time to ascertain viral load and the efficacy of drug therapy.

Patients infected with Ebola produce antibodies or IgG specific to Ebola. Ebola IgG have been identified and are currently used via ELISA and RT-PCR to detect Ebola infection. This assay allows for known Ebola IgG to be subjected to an oxidating agent Step 220 (FIG. 5) so that Ebola IgG can be employed as binding agent 335. Ebola IgG binding agent 335 will bind with Ebola virus present in a patient's sample so that this assay will detect the presence of Ebola in an infected patient. If a patient is not infected with Ebola, then Ebola IgG binding agent 335 will not bind with agents in a patient's sample. Thus, values for a cantilever test sensor 104 will be unchanged when subjected to a patient sample not infected with Ebola. And, the electrical resonance/resistance value for cantilever test sensor 104 will change during this assay if a patient's sample is infected with Ebola virus.

Figure 26:
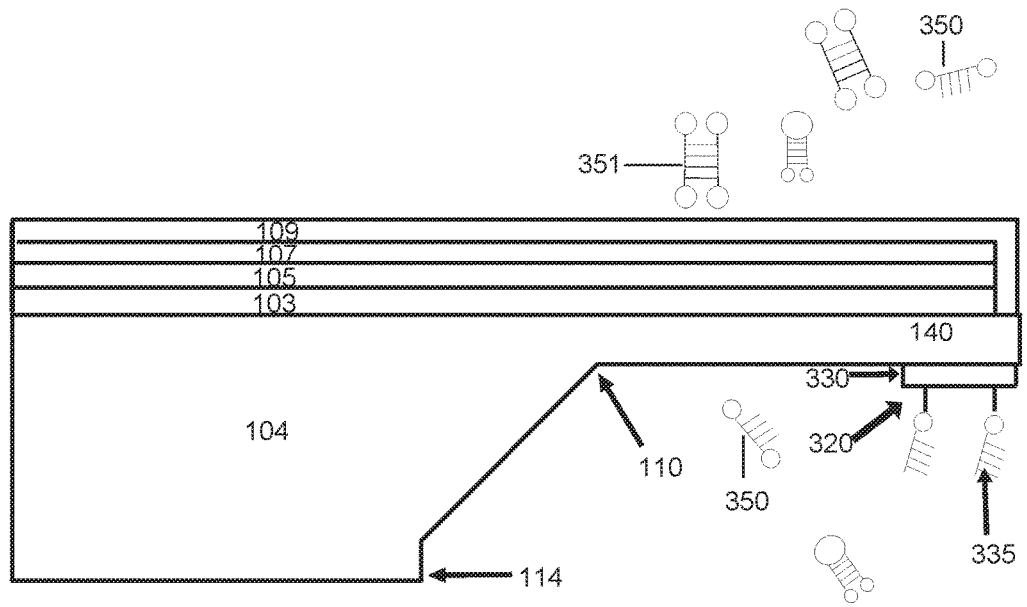
FIG. 26 illustrates the PEMS microcantilever test sensor with ctDNA as the binding agent. This is the sensor shown in FIG. 19.
Figure 27:
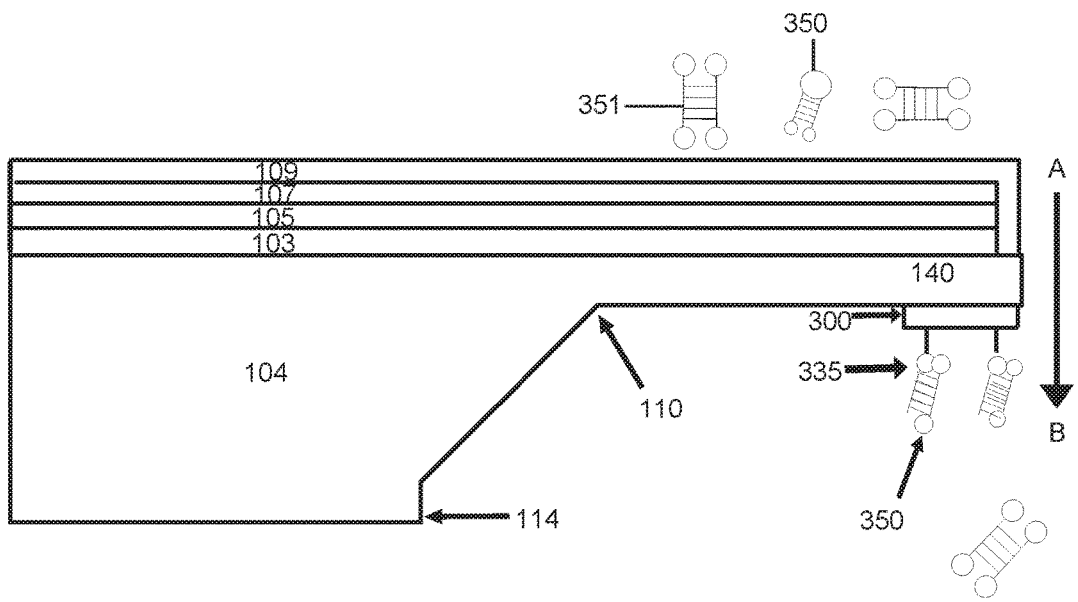
FIG. 27 illustrates the binding of ctDNA to the test sensor with ctDNA complimentary to ctDNA, wherein the ctDNA is indicative of a cancerous genetic mutation.

FIGS. 26 and 27 is an exemplary embodiment illustrating single-stranded ctDNA binding agent 335 binding to cantilever beam 140. In FIG. 26, an aqueous solution containing both complimentary single-stranded ctDNA 350 and other DNA/RNA components 351 are shown. ctDNA binding agent 335 only binds with complimentary single-stranded ctDNA 350. FIG. 27 depicts the binding of ctDNA 350 with ctDNA binding agent 335. In FIG. 27, ctDNA 350 a base within the ctDNA 350 sequence binds/bonds with its complimentary base within ctDNA binding agent 335 via hydrogen bonding. The cumulative effect of base pairing between ctDNA 350 and ctDNA binding agent 335 adds weight to the surface of binding area 330 on the underside of the PEMS cantilever test sensor 104, causing the PEMS cantilever test sensor 104 to move in the "A" and/or "B" direction upon binding of ctDNA. Beam 140 moves about hinge 110 relative to base 114 in the "A" and/or "B" direction This movement of beam 140 creates a resonance/resistance change that can be calculated electrically by processor 420. Only complimentary ctDNA will bind to ctDNA binding agent 335. Non-complimentary single-stranded ctDNA will not bind with ctDNA binding agents. This test is highly specific in that only ctDNA including the mutation expressed in the ctDNA binding agent will bind forming stable double-stranded ctDNA. Test well 4 may be heated, or the patient specimen heated, to cause the double stranded DNA to separate into single DNA strands to increase the concentration of ssDNA within the patient specimen.

I hereby claim:

1. A method of attaching a RNA sequence to a piezoelectric microcantilever sensor, the method comprising:
    oxidizing a RNA sequence that is an anti-sense compliment to a RNA sequence to be detected in an aqueous sample to result in the formation of at least one aldehyde functional group or at least one ketone functional group at the 3' terminus of the RNA sequence, creating an alkoxyamine functional group on a surface of the piezoelectric microcantilever sensor;

bonding the 3' terminus of the RNA sequence to the alkoxyamine functional group on the surface of the piezoelectric microcantilever forming an oxime bond between an oxidized carbon atom of the at least one aldehyde functional group or at least one ketone functional group at the 3' terminus of the RNA sequence and a nitrogen atom of the alkoxyamine functional group on the surface of the piezoelectric microcantilever sensor; and wherein the surface of the piezoelectric microcantilever sensor is composed of silicon or silicon nitride, wherein the silicon or silicon nitride surface of the piezoelectric microcantilever sensor has been modified prior to creating the alkoxyamine functional group on the surface of the piezoelectric microcantilever sensor so that the piezoelectric microcantilever sensor surface includes at least one nitrogen atom that has been bonded to the silicon or silicon nitride surface of the piezoelectric microcantilever sensor.

2. The method of claim 1 wherein an alkoxyamine functional group is created on a surface of the piezoelectric microcantilever sensor by performing the following steps:
a binding area on the surface of the piezoelectric microcantilever sensor is treated with an oxidizing agent creating one or more silanol residues on the binding area;
the one or more silanol residues are treated with a silane coupling agent creating one or more primary amine functional groups on the binding area;
the one or more primary amine functional groups are treated with gluteraldehyde adding one or more aldehyde functional groups to the one or more primary amine functional groups; and
the one or more aldehyde functional groups is treated with hydroxylamine creating one or more alkoxyamine functional groups on the surface of the piezoelectric microcantilever sensor.

3. The device of claim 1, further comprising arranging two or more piezoelectric microcantilever sensors into a cantilever array, wherein the cantilever array includes at least one reference piezoelectric microcantilever sensor and at least one test piezoelectric microcantilever sensor, wherein the reference piezoelectric microcantilever sensor lacks a bound nucleic acid molecule, and wherein the test piezoelectric microcantilever sensor includes at least one bound nucleic acid molecule.

4. The method of claim 1, wherein the RNA sequence to be detected includes a sequence of HIV RNA, HCV RNA, Ebola RNA, or VHF RNA.

5. A method of attaching a ctDNA sequence to a piezoelectric microcantilever sensor, the method comprising:
oxidizing a ctDNA sequence that is the anti-sense compliment to a ctDNA sequence to be detected in an aqueous sample resulting in the formation of at least one aldehyde functional group or at least one ketone functional group at the 3' terminus of the ctDNA sequence,
creating an alkoxyamine functional group on a surface of the piezoelectric microcantilever sensor;
bonding the 3' terminus of the ctDNA sequence to the alkoxyamine functional group on the surface of the piezoelectric microcantilever sensor forming an oxime bond between an oxidized carbon atom of the at least one aldehyde functional group or at least one ketone functional group at the 3' terminus of the ctDNA sequence and a nitrogen atom of the alkoxyamine functional group on the surface of the piezoelectric microcantilever sensor; and wherein the surface of the piezoelectric microcantilever sensor is composed of silicon or silicon nitride, wherein the silicon or silicon nitride surface of the piezoelectric microcantilever sensor has been modified prior to creating the alkoxyamine functional group on the surface of the piezoelectric microcantilever sensor so that the piezoelectric microcantilever sensor surface includes at least one nitrogen atom that has been bonded to the silicon or silicon nitride surface of the piezoelectric microcantilever sensor.

6. A method of attaching a cfDNA sequence to a piezoelectric microcantilever sensor, the method comprising:
oxidizing a cfDNA sequence that is the anti-sense compliment to a cfDNA sequence to be detected in an aqueous sample resulting in the formation of at least one aldehyde functional group or at least one ketone functional group at the 3' terminus of the cfDNA sequence,
creating an alkoxyamine functional group on a surface of the piezoelectric microcantilever sensor;
bonding the 3' terminus of the cfDNA sequence to the alkoxyamine functional group on the surface of the piezoelectric microcantilever sensor forming an oxime bond between an oxidized carbon atom of the at least one aldehyde functional group or at least one ketone functional group at the 3' terminus of the cfDNA sequence and a nitrogen atom of the alkoxyamine functional group on the surface of the piezoelectric microcantilever sensor; and wherein the surface of the piezoelectric microcantilever sensor is composed of silicon or silicon nitride, wherein the silicon or silicon nitride surface of the piezoelectric microcantilever sensor has been modified prior to creating the alkoxyamine functional group on the surface of the piezoelectric microcantilever sensor so that the piezoelectric microcantilever sensor surface includes at least one nitrogen atom that has been bonded to the silicon or silicon nitride surface of the piezoelectric microcantilever sensor.

7. The compound having the structure:

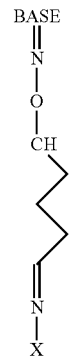

wherein Base is a purine or pyrimidine base of a nucleic acid molecule that has been oxidized at a hydroxyl functional group on a 3' terminus ribose moiety to create at least one aldehyde functional group or at least one ketone functional group; and X is a silicon or silicon nitride surface of a piezoelectric microcantilever sensor.

\* \* \* \* \*